United States Patent [19]

Plana Duran et al.

[11] Patent Number: 5,888,513
[45] Date of Patent: Mar. 30, 1999

[54] RECOMBINANT PRRSV PROTEINS, DIAGNOSTIC KITS AND VACCINES CONTAINING SUCH RECOMBINANT PRRSV PROTEINS

[75] Inventors: Juan Plana Duran, Vall de Bianya; Jose Ignacio Casal Alvarez, Madrid; Isabel Climent Sanchez, Vall de Bianya, all of Spain

[73] Assignee: Cyanamid Iberica, S.A., Madrid, Spain

[21] Appl. No.: 578,614

[22] Filed: Apr. 8, 1996

[30] Foreign Application Priority Data

May 13, 1994 [ES] Spain ................................. 9401027
Apr. 27, 1995 [ES] Spain ................................. 9500815

[51] Int. Cl.$^6$ .......................... A61K 39/00; A61K 39/12; C12N 15/00; C12N 7/00
[52] U.S. Cl. ..................... 424/186.1; 424/201.1; 424/198.1; 424/204.1; 424/278.1; 424/199.1; 424/815; 435/235.1; 435/5; 435/69.3; 435/325; 435/252.3; 435/91.1; 435/239; 530/350; 536/23.72
[58] Field of Search ............................. 424/199.1, 815, 424/176.1, 186.1, 201.1, 177.1, 278.1, 198.1, 704.1; 435/235.1, 7.92, 7.95, 91.1, 5, 252.3, 239–325, 320.1; 530/350; 536/23.72

[56] References Cited

FOREIGN PATENT DOCUMENTS

| | | |
|---|---|---|
| 0 529 584 A2 | 3/1993 | European Pat. Off. . |
| 0 541 418 A1 | 5/1993 | European Pat. Off. . |
| 0595436 | 4/1994 | European Pat. Off. ........ A61K 39/12 |
| 0 601 062 B1 | 6/1994 | European Pat. Off. . |
| 0 610 250 B1 | 8/1994 | European Pat. Off. . |
| 9221375 | 10/1992 | WIPO ............................ A61K 39/12 |
| WO 93/14196 | 6/1993 | WIPO . |

OTHER PUBLICATIONS

Luckow, et al., 1988, Biotech., vol. 6, pp. 47–55.
Conzelmann, et al., 1993, Virology, vol. 193, No. 1, pp. 329–339.
S. J. McCullough, et al., The New Pig Disease, Porcine Respiration and Reproductive Syndrome, A Report on the Seminar/Workshop Held in Brussels on 29–30 Apr. 1991 and Organized by the European Commission (Directorate-General for Agriculture), 46–52.
von V.F. Ohlinger, et al., Der Seuchenhafte Spätabort beim Schwein—Ein Beitrag zur Ätiologie des Porcine Reproductive and Respiratory Syndrome (PRRS), Tierärztl. Umschau 46, 703–708 (1991).

James E. Collins, et al., Swine Infertility and Respiratory Syndrome (Mystery Swine Disease), Proc. Minnesota Conf. for Veterinarians, Sep. 15, 1991–Sep. 17, 1991, 200–205.

G. Wensvoort, et al., Mystery swine disease in the Netherlands: the isolation of Lelystad virus, The Veterinary Quarterly, vol. 13, No. 3, 1991, 121–129.

Gert Wensvoort, et al., Lelystad virus, the cause of porcine epidemic abortion and respiratory syndrome: a review of mystery swine disease research at Lelystad, Veterinary Microbiology, 33(1992), 185–193.

C. Terpstra, et al., Experimental reproduction of porcine epidemic abortion and respiratory syndrome (mystery swine disease) by infection with Lelystad virus: Koch's postulates fulfilled, The Veterinary Quarterly, vol. 13, No. 3, 1991, 131–136.

J.M.A. Pol, et al., Pathological, ultrastructural, and immunohistochemical changes caused by Lelystad virus in experimentally induced infections of mystery swine disease (synonym: porcine epidemic abortion and respiratory syndrome (PEARS)), The Veterinary Quarterly, vol. 13, No. 3, 137–143 (Jul. 1991).

D.J. Paton, et al., Isolation of a Lelystad virus–like agent from British pigs and scanning electron microscopy of infected macrophages, Veterinary Microbiology, 33 (1992), 195–201.

Joan Plana, et al., Porcine epidemic abortion and respiratory syndrome (mystery swine disease). Isolation in Spain of the causative agent experimental reproduction of the disease, Veterinary Microbiology 33 (1992) 203–211.

*Primary Examiner*—Mary E. Mosher
*Assistant Examiner*—Ali R. Salimi
*Attorney, Agent, or Firm*—Gale Matthews; Milagros A. Cepeda

[57] ABSTRACT

Recombinant proteins of the causative virus of porcine reproductive and respiratory syndrome (PRRS), corresponding to ORFs 2 to 7 of the PRRSV Spanish isolate (PRRS-Olot), have been produced in baculovirus expression system using Sf9 cell cultures as a permissive host. These recombinant proteins are suitable for the formulation of vaccines capable of efficaciously protecting porcine livestock from PRRS and for the preparation of diagnostic kits adequate for detection of anti-PRRSV antibodies as well as of PRRSV in a pig biological sample. This invention is of interest to Veterinary Medicine.

52 Claims, 20 Drawing Sheets

```
        10         20         30         40         50         60
GAATTGCAGG TAGAGCTAGG TAAACCCCGG CTGCCGCCTG AGCAAGTGCC GTGAATCCGA
        70         80         90        100        110        120
AGTGATGCAA TGGGGTCACT GTGGAGCAAA ATCAGCCAGC TGTTCGTGGA CGCCTTCACT
       130        140        150        160        170        180
GAGTTCCTTG TTAGTGTGGT TGACATTGTC ATTTTCCTTG CCATACTGTT TGGGTTCACC
       190        200        210        220        230        240
GTTGCCGGCT GGTTACTGGT CTTTCTTCTC AGAGTGGTTT GCTCCGCGCT TCTCCGTTCG
       250        260        270        280        290        300
CGCTCTGCCA TTCACTCTCC CGAACTATCG AAGGTCCTAT GAAGGCTTGT TACCCAATTG
       310        320        330        340        350        360
CAGACCGGAT GTCCCACAAT TCGCTGTCAA GCACCCATTG GGTATGTTTT GGCACATGCG
       370        380        390        400        410        420
AGTCTCCCAC CTAATTGATG AAATGGTCTC TCGTCGCATT TACCAGACCA TGGAACATTC
       430        440        450        460        470        480
AGGTCAAGCG GCCTGGAAGC AGGTGGTTAG TGAGGCCACT CTTACAAAGC TGTCAGGACT
       490        500        510        520        530        540
TGATATAGTT ACTCATTTCC AACACCTGGC CGCAGTGGAG GCGGATTCTT GCCGCTTTCT
       550        560        570        580        590        600
CAGCTCACGA CTTGTGATGC TAAAAAATCT TGCCGTTGGC AATGTGAGCC TACAGTACAA
       610        620        630        640        650        660
CACCACGTTA GACCGCGTTG AGCTCATCTT CCCTACGCCG GGTACGAGGC CCAAGTTGAC
       670        680        690        700        710        720
CGATTTCAGA CAATGGCTCA TCAGTGTGCA CGCTTCCATT TTTTCCTCTG TAGCTTCATC
       730        740        750        760        770        780
TGTTACCTTG TTCATAGTGC TTTGGCTTCG AATTCCAATT CTACGCTATG TTTTTGGTTT
```

FIG.1A

```
       790        800        810        820        830        840
CCATTGGCCC ACGGCAACAC ATCATTCGAG CTAACCATCA ACTACACCAT ATGTATGCCC
       850        860        870        880        890        900
TGCTCTACCA GTCAAGCGGC TCACCAAAGA CTCGAGCCCG GTCGTAACAT GTG9TGCAGA
       910        920        930        940        950        960
ATAGGGCACG ACAGGTGTGA GGAACGTGAC CATGATGAGT TGTCAATGTC CATTCCGTCT
       970        980        990       1000       1010       1020
GGGTACGATA ACCTCAAACT TGAGGGTTAT TATGCTTGGC TGGCCTTTTT GTCCTTTTCC
      1030       1040       1050       1060       1070       1080
TACGCGGCCC AATTCCATCC GGAGTTGTTC GGAATAGGAA ACGTGTCGCG CGTCTTCGTG
      1090       1100       1110       1120       1130       1140
GACAAGCAAC ACCAGTTCAT TTGCGCCGAG CATGATGGAC GAAATTCAAC CATATCTACC
      1150       1160       1170       1180       1190       1200
GAATATAACA TCTCCGCATT ATATGCGTCG TACTACCATC ACCAAATAGA CGGGGGCAAC
      1210       1220       1230       1240       1250       1260
TGGTTCCATT TGGAATGGCT GCGGCCATTC TTTTCCTCCT GGCTGGTGCT CAACATTTCA
      1270       1280       1290       1300       1310       1320
TGGTTTCTGA GGCGTCCGCC TGTAAGCCCT GTTTCTCGAC GCATCTATCA GATATTAAGA
      1330       1340       1350       1360       1370       1380
CCAACACGAC CGCGGCTGCC GGTTTCATGG TCCTTCAGAA CATCAATTGT CTCCGACCTC
      1390       1400       1410       1420       1430       1440
ACGGGGTCTC AACAGCGCAA GAGAACATTT CCTTCGGGAA GCCGTCTCAA TGTCGTGAAG
      1450       1460       1470       1480       1490       1500
CCGTCGGTAT TCCCCAGTAC ATTACGATAA CGGCTAATGT GACCGATGAA TCGTATTTGT
      1510       1520       1530       1540       1550       1560
ACAACGCGGA CTTGCTGATG CTTTCTGCGT GCCTTTTCTA CGCTTCAGAA ATGAGCGAAA
```

FIG. 1B

```
      1570       1580       1590       1600       1610       1620
AAGGCTTCAA AGTTATCTTT GGGAACGTCT CTGGCGTTGT TTCTGCTTGT GTCAATTTTA
      1630       1640       1650       1660       1670       1680
CAGATTATGT GGCCCATGTG ACCCAACATA CCCAGCAGCA TCATCTGGTA ATTCATCACA
      1690       1700       1710       1720       1730       1740
TTCGGTTGCT GCATTTCTTG ACACCATCTA CAATGAGGTG GGCTACAACC ATTGCTTGTT
      1750       1760       1770       1780       1790       1800
TGTTCGCCAT TCTCTTGGCG ATATGAGATG TTCTCACAAA TTGGGGCGTT TCTTGACTCC
      1810       1820       1830       1840       1850       1860
TCACTCTTGC TTCTGGTGGC TTTTTTTGCT GTGTACCGGC TTGTCCTGGT CCTTTGTCGC
      1870       1880       1890       1900       1910       1920
TGGCGGCAGC AGCTCGACAT ACCAATACAT ATATAACTTA ACGATATGCG AGCTGAATGG
      1930       1940       1950       1960       1970       1980
GACCGACTGG TTGTCCAACC ATTTTGATTG GGCAGTCGAG ACCTTTGTGC TTTACCCGGT
      1990       2000       2010       2020       2030       2040
TGCCACTCAT ATCCTCTCAC TGGGTTTTCT CACAACAAGC CATTTTTTTG ACGCGCTCGG
      2050       2060       2070       2080       2090       2100
TCTCGGCGCT GTGTCCACTA TAGGATTTGT TGGCGGGCGG TATGTACTCA GCAGCGTGTA
      2110       2120       2130       2140       2150       2160
CGGCGCTTGT GCTTTCGCAG CGTTCGTATG TTTTGTCATC CGTGCTGTTA AAAATTGCAT
      2170       2180       2190       2200       2210       2220
GGCTTTCCGC TATGCCCACA CCCGGTTTAC CAACTTCATT GTGGACGACC GGGGGAGAAT
      2230       2240       2250       2260       2270       2280
CCATCGGTGG AAGTCTCCAA TAGTGGTAGA GAAATTGGGC AAAGCTGAAG TCGGTGGCGA
      2290       2300       2310       2320       2330       2340
CCTTGTCACC ATCAAACATG TCGTCCTCGA AGGGGTTAAA GCTCAACCCT TGACGAGGAC
```

FIG. 1C

```
       2350       2360       2370       2380       2390       2400
TTCGGCTGAG CAATGGGAAG CCTAGACGAT TTTTGCAATG ATTCTACCGC CGCACAAAAG
       2410       2420       2430       2440       2450       2460
CTTGTGCTAG CCTTTAGCAT TACATATACA CCTATAATGA TATACGCCCT TAAGGTGTCA
       2470       2480       2490       2500       2510       2520
CGCGGCCGAC TCCTGGGGCT GTTGCACATC CTAATATTCC TGAATTGTTC TTTCACATTC
       2530       2540       2550       2560       2570       2580
GGATACATGA CATATGTGCG TTTTCAATCC ACCAACCGTG TCGCACTTAC TCTGGGGGCT
       2590       2600       2610       2620       2630       2640
GTTGTCGCCC TTCTGTGGGG TGTTTACAGC TTCACAGAGT CATGGAAGTT TGTTACTTCC
       2650       2660       2670       2680       2690       2700
AGATGCAGAT TGTGTTGCCT AGGCCGGCGA TACATTCTGG CCCCTGCCCA TCACGTAGAA
       2710       2720       2730       2740       2750       2760
AGTGCTGCAG GTCTCCATTC AATCCCAGCG TCTGGTAACC GAGCATACGC TGTCAGAAAG
       2770       2780       2790       2800       2810       2820
CCCGGACTAA CATCAGTGAA CGGCACTCTA GTTCCAGGAC TTCGGAGCCT CGTGCTGGGC
       2830       2840       2850       2860       2870       2880
GGCAAACGAG CTGTTAAACG AGGAGTGGTT AACCTCGTCA AGTATGGCCG GTAAAAACCA
       2890       2900       2910       2920       2930       2940
GAGCCAGAAG AAAAAGAAAA GTGCAGCTCC GATGGGGAAT GGCCAGCCAG TCAATCAACT
       2950       2960       2970       2980       2990       3000
GTGCCAGTTG CTGGGTGCAA TGATAAAGTC CCAGCGCCAG CAACCTAGGG GAGGACAGGC
       3010       3020       3030       3040       3050       3060
CAAAAAGAAA AAGCCTGAGA AGCCACATTT TCCCTTAGCT GCTGAAGATG ACATCCGGCA
       3070       3080       3090       3100       3110       3120
CCACCTCACC CAGACCGAAC GTTCCCTCTG CTTGCAATCG ATCCAGACGG CTTTTAATCA
```

FIG. 1D

```
           3130       3140       3150       3160       3170       3180
     AGGCGCAGGA ACTGCGTCGC TTTCATCCAG CGGGAAGGTC AGTTTTCAGG TTGAGTTCAT
           3190       3200       3210       3220       3230       3240
     GCTGCCGGTT GCTCATACGG TGCGCCTGAT TCGCGTGACT TCTACATCCG CCACTCAGGG
           3250       3260       3270       3280       3290       3300
     TGCAAGCTAA TTTGACAGTC AGGTGAATGG CCGCGATTGA CGTGTGGCCT CTAAGTCACC
           3310       3320       3330       3340       3350       3360
     TATTCAATTA GGGCGATCAC ATGGGGGTCA AACTTAATCA GGCAGGAACC ATGTGACCGA
           3370       3380
     AATTAAAAAA AAAAAAAAAA AAA
```

FIG.1E

ORF2

Met Gln Trp Gly His Cys Gly Ala Lys Ser Ala Ser Cys Ser Trp Thr
1              5                   10              15

Pro Ser Leu Ser Ser Leu Leu Val Trp Leu Thr Leu Ser Phe Ser Leu
            20                  25              30

Pro Tyr Cys Leu Gly Ser Pro Leu Pro Ala Gly Tyr Trp Ser Phe Phe
        35                  40                  45

Ser Glu Trp Phe Ala Pro Arg Phe Ser Val Arg Ala Leu Pro Phe Thr
    50                  55                  60

Leu Pro Asn Tyr Arg Arg Ser Tyr Glu Gly Leu Leu Pro Asn Cys Arg
65              70                  75                      80

Pro Asp Val Pro Gln Phe Ala Val Lys His Pro Leu Gly Met Phe Trp
                85                  90                  95

His Met Arg Val Ser His Leu Ile Asp Glu Met Val Ser Arg Arg Ile
            100             105             110

Tyr Gln Thr Met Glu His Ser Gly Gln Ala Ala Trp Lys Gln Val Val
        115             120             125

Ser Glu Ala Thr Leu Thr Lys Leu Ser Gly Leu Asp Ile Val Thr His
    130             135             140

Phe Gln His Leu Ala Ala Val Glu Ala Asp Ser Cys Arg Phe Leu Ser
145             150             155

Ser Arg Leu Val Met Leu Lys Asn Leu Ala Val Gly Asn Val Ser Leu
            165             170             175

Gln Tyr Asn Thr Thr Leu Asp Arg Val Glu Leu Ile Phe Pro Thr Pro
            180             185             190

Gly Thr Arg Pro Lys Leu Thr Asp Phe Arg Gln Trp Leu Ile Ser Val
        195             200             205

His Ala Ser Ile Phe Ser Ser Val Ala Ser Ser Val Thr Leu Phe Ile
    210             215             220

Val Leu Trp Leu Arg Ile Pro Ile Leu Arg Tyr Val Phe Gly Phe His
225             230             235             240

Trp Pro Thr Ala Thr His His Ser Ser
                245

FIG.2A

ORF3

Met Ala His Gln Cys Ala Arg Phe His Phe Leu Cys Ser Phe Ile
1              5                   10                  15

Cys Tyr Leu Val His Ser Ala Leu Ala Ser Asn Ser Asn Ser Thr Leu
            20                  25                  30

Cys Phe Trp Phe Pro Leu Ala His Gly Asn Thr Ser Phe Glu Leu Thr
        35                  40                  45

Ile Asn Tyr Thr Ile Cys Met Pro Cys Ser Thr Ser Gln Ala Ala His
    50                  55                  60

Gln Arg Leu Glu Pro Gly Arg Asn Met Trp Cys Arg Ile Gly His Asp
65              70                  75                      80

Arg Cys Glu Glu Arg Asp His Asp Glu Leu Ser Met Ser Ile Pro Ser
            85                  90                  95

Gly Tyr Asp Asn Leu Lys Leu Glu Gly Tyr Tyr Ala Trp Leu Ala Phe
            100                 105                 110

Leu Ser Phe Ser Tyr Ala Ala Gln Phe His Phe Glu Leu Phe Gly Ile
        115                 120                 125

Gly Asn Val Ser Arg Val Phe Val Asp Lys Gln His Gln Phe Ile Cys
    130                 135                 140

Ala Glu His Asp Gly Arg Asn Ser Thr Ile Ser Thr Glu Tyr Asn Ile
145                 150                 155                 160

Ser Ala Leu Tyr Ala Ser Tyr Tyr His His Gln Ile Asp Gly Gly Asn
                165                 170                 175

Trp Phe His Leu Glu Trp Leu Arg Pro Phe Phe Ser Ser Trp Leu Val
        180                 185                 190

Leu Asn Ile Ser Trp Phe Leu Arg Arg Ser Pro Val Ser Pro Val Ser
        195                 200                 205

Arg Arg Ile Tyr Gln Ile Leu Arg Pro Thr Arg Pro Arg Leu Pro Val
        210                 215                 220

Ser Trp Ser Phe Arg Thr Ser Ile Val Ser Asp Leu Thr Gly Ser Gln
225                 230                 235                 240

Gln Arg Lys Arg Thr Phe Pro Ser Gly Ser Arg Leu Asn Val Val Lys
            245                 250                 225

Pro Ser Val Phe Pro Ser Thr Leu Arg
            260                 265

FIG.2B

ORF4

Met Ala Ala Ala Ile Leu Phe Leu Leu Ala Gly Ala Gln His Phe Met
1               5                   10                  15

Val Ser Glu Ala Phe Ala Cys Lys Pro Cys Phe Ser Thr His Leu Ser
            20                  25                  30

Asp Ile Lys Thr Asn Thr Thr Ala Ala Ala Gly Phe Met Val Leu Gln
            35                  40                  45

Asn Ile Asn Cys Leu Arg Pro His Gly Val Ser Thr Ala Gln Glu Asn
        50                  55                  60

Ile Ser Phe Gly Lys Pro Ser Gln Cys Arg Glu Ala Val Gly Ile Pro
65              70                  75                      80

Gln Tyr Ile Thr Ile Thr Ala Asn Val Thr Asp Glu Ser Tyr Leu Tyr
                85                  90                  95

Asn Ala Asp Leu Leu Met Leu Ser Ala Cys Leu Phe Tyr Ala Ser Glu
            100                 105                 110

Met Ser Glu Lys Gly Phe Lys Val Ile Phe Gly Asn Val Ser Gly Val
            115                 120                 125

Val Ser Ala Cys Val Asn Phe Thr Asp Tyr Val Ala His Val Thr Gln
    130                 135                 140

His Thr Gln Gln His His Leu Val Ile Asp His Ile Arg Leu Leu His
145                 150                 155

Phe Leu Thr Pro Ser Thr Met Arg Trp Ala Thr Thr Ile Ala Cys Leu
                165                 170                 175

Phe Ala Ile Leu Leu Ala Ile
            180

FIG.2C

ORF5

Met Arg Cys Ser His Lys Leu Gly Arg Phe Leu Thr Pro His Ser Cys
 1            5                  10                 15

Phe Trp Trp Leu Phe Leu Leu Cys Thr Gly Leu Ser Trp Ser Phe Val
            20                  25                 30

Ala Gly Gly Ser Ser Ser Thr Tyr Gln Tyr Ile Tyr Asn Leu Thr Ile
         35                  40                  45

Cys Glu Leu Asn Gly Thr Asp Trp Leu Ser Asn His Phe Asp Trp Ala
     50                  55                  60

Val Glu Thr Phe Val Leu Tyr Pro Val Ala Thr His Ile Leu Ser Leu
 65                  70                  75

Gly Phe Leu Thr Thr Ser His Phe Phe Asp Ala Leu Gly Leu Gly Ala
             85                  90                  95

Val Ser Thr Ile Gly Phe Val Gly Gly Arg Tyr Val Leu Ser Ser Val
         100                 105                 110

Tyr Gly Ala Cys Ala Phe Ala Ala Phe Val Cys Phe Val Ile Arg Ala
         115                 120                 125

Val Lys Asn Cys Met Ala Cys Arg Tyr Ala His Thr Arg Phe Thr Asn
     130                 135                 140

Phe Ile Val Asp Asp Arg Gly Arg Ile His Arg Trp Lys Ser Pra Ile
145                 150                 155                 160

Val Val Glu Lys Leu Gly Lys Ala Glu Val Gly Gly Asp Leu Val Thr
             165                 170                 175

Ile Lys His Val Val Leu Glu Gly Val Lys Ala Gln Pro Leu Thr Arg
             180                 185                 190

Thr Ser Ala Glu Gln Trp Glu Ala
         195                 200

FIG.2D

ORF6

Met Gly Ser Leu Asp Asp Phe Cys Asn Asp Ser Thr Ala Ala Gln Lys
 1           5               10              15

Leu Val Leu Ala Phe Ser Ile Thr Tyr Thr Pro Ile Met Ile Tyr Ala
            20              25              30

Leu Lys Val Ser Arg Gly Arg Leu Leu Gly Leu Leu His Ile Leu Ile
            35              40              45

Phe Leu Asn Cys Ser Phe Thr Phe Gly Tyr Met Thr Tyr Val Arg Phe
     50              55              60

Gln Ser Thr Asn Arg Val Ala Leu Thr Leu Gly Ala Val Val Ala Leu
 65              70              75

Leu Trp Gly Val Tyr Ser Phe Thr Glu Ser Trp Lys Phe Val Thr Ser
                85              90              95

Arg Cys Arg Leu Cys Cys Leu Gly Arg Arg Tyr Ile Leu Ala Pro Ala
            100             105             110

His His Val Glu Ser Ala Ala Gly Leu His Ser Ile Pro Ala Ser Gly
        115             120             125

Asn Arg Ala Tyr Ala Val Arg Lys Pro Gly Leu Thr Ser Val Asn Gly
        130             135             140

Thr Leu Val Pro Gly Leu Arg Ser Leu Val Leu Gly Gly Lys Arg Ala
145             150             155             160

Val Lys Arg Gly Val Val Asn Leu Val Lys Tyr Gly Arg
                165             170

FIG.2E

ORF7

Met Ala Gly Lys Asn Gln Ser Gln Lys Lys Lys Ser Ala Ala Pro
 1               5              10              15

Met Gly Asn Gly Gln Pro Val Asn Gln Leu Cys Gln Leu Leu Gly Ala
            20              25              30

Met Ile Lys Ser Gln Arg Gln Gln Pro Arg Gly Gly Gln Ala Lys Lys
            35              40              45

Lys Lys Pro Glu Lys Pro His Phe Pro Leu Ala Ala Glu Asp Asp Ile
    50              55              60

Arg His His Leu Thr Gln Thr Glu Arg Ser Leu Cys Leu Gln Ser Ile
65              70              75              80

Gln Thr Ala Phe Asn Gln Gly Ala Gly Thr Ala Ser Leu Ser Ser Ser
            85              90              95

Gly Lys Val Ser Phe Gln Val Glu Phe Met Leu Pro Val Ala His Thr
            100             105             110

Val Arg Leu Ile Arg Val Thr Ser Thr Ser Ala Ser Gln Gly Ala Ser
            115             120             125

FIG.2F

RECOMBINANT PRRSV PROTEINS, DIAGNOSTIC KITS AND VACCINES CONTAINING SUCH RECOMBINANT PRRSV PROTEINS

SCOPE OF THE INVENTION

This invention relates to viral recombinant proteins of the causative agent of porcine reproductive and respiratory syndrome (PRRS) produced in an expression system of recombinant baculoviruses multiplied in permissive host cell culture. The invention also relates to diagnostic kits and vaccines which comprise, at least, one of the said recombinant proteins.

HISTORY OF THE INVENTION

In Spain, the first cases of respiratory alterations in piglets were detected in a 300-piglet batch imported from Germany, in mid-January 1991 (Plana et al., Med. Vet., Vol. 8, No. 11, 1991). Shortly afterwards, in two breeding herds on two farms situated near the herd where the initial problem had appeared, a disease was detected characterized by an abnormally high number of abortions during the last phase of gestation, as well as 70% mortality in piglets.

The cause of these epizootic outbreaks was not known, but their symptomatology was similar to the clinical signs that had been described for a swine disease first detected in Europe in Germany (1990), and to the disease denominated Mystery Swine Disease detected in the United States and Canada in 1987 (Hill, Proceedngs of the Mystery Swine Disease Committee Meeting, Oct. 6, 1990, Denver, USA). This disease affects pregnant sows, provoking in them anorexia, abortions, stillbirths, mummified fetuses, weak piglets that die in a few hours of life, and post-farrowing respiratory problems, among others. At present, the disease is known as "Porcine Reproductive and Respiratory Syndrome" (PRRS), although it was previously referred to as "Blue-eared Pig Disease", "Mysterious Reproductive Syndrome" (MRS), "Swine Infertility and Respiratory Syndrome" (SIRS) and "Porcine Epidemic Abortion and Respiratory Syndrome" (PEARS).

At present, it is known that the causative agent of this disease is a virus denominated as PRRS virus (PRRSV). This virus was isolated for the first time in the Netherlands by a group of researchers of the CDI/Lelystad, who denominated it as Lelystad virus (LV) (Wesvoort, G et al., Vet. Quarterly, Vol 3, 121–130, 1991). Some months later, another isolate was obtained in Spain by Laboratorios Sobrino/Cyanamid (Plana et al., Vet. Microbiol., 33:203.211, 1992), which will be identified in this description as PRRS-Olot. From that time, new isolates of this virus have been described (EP application No. 0 529 584 A2, PCT application Nos. WO 93/06211 and WO 93/07898).

The structural characteristics of the PRRS virus have been described in two recent publications:

a) Meulenberg, J. J. M., et al., "Lelystad virus, the causative agent of porcine epidemic abortion and respiratory syndrome (PEARS), is related to LDV and EAV". Virology, 192: 62–72, (1993); and b) Cozelmann, K-K., et al., "Molecular characterization of porcine reproductive and respiratory syndrome virus, a member of the Arterivirus group". Virology, 193: 329–339, (1993).

The PRRS virus has a size of 50–60 nm, with an envelope of of approximately 30–35 nm contained in the nucelocapsid, and a single RNA molecule as genomic material. Based on these morphological data, PRRSV was initially classified as a Togavirus, although based on its genomic structure and transcription and translation mechanisms it was closer to the Coronaviridae family. Recently, and based on differences and/or similarities in comparison with the previous groups, its classification was proposed within a new family denominated Arteriviridae (Cavanagh D., et al., Arch. Virology, 1994). Together with PRRSV, in this group are included the equine arteritis viruses (EAV), lactic dehydrogenase virus (LDV) and simian hemorrhagic fever virus (SHFV).

Recently, the entire Lelystad virus (LV) genome (Meulenberg et al., quoted above), a genomic segment of the Tübingen (Germany) PRRS virus isolate (TV)(Cozelmann et al., quoted above), and a segment of the PRRS-Olot virus (Spanish Patent claim no. ES P9301973) were cloned and sequenced. Based on all the results obtained it can be stated that the PRRSV genome is made up of a single strand RNA molecule which contains at 3' end a poly-A tail. The length of the genome is of approximately 15000 base pairs (bp), and in its structure it contains seven open reading frames (ORFs) coding for the viral proteins. The ORFs have been denominated as ORF1 to ORF7 and they show small overlapping segments between them. It has been propounded that synthesis of the viral proteins is produced from a group of different length subgenomic transcripts (mRNA), but of similar 3' polyadenylated end, and 5' leader sequence originating from the non-coding 5' end sequence. This form of viral protein expression has been denominated as nested mRNAs and has been previously described for coraniviruses (Spaan, W. J. M., Cavanagh, D., and Horzineck, M. C., J. Gen. Virol., 69:2939–2952, 1988). Based on the Lelystad (LV) and Tubingen (TV) PRRSV viral isolate nucleotide sequence, and by homology with what has been observed with other arteriviruses, it has been propounded that in the viral genome, ORF1 (a and b) code for viral polymerase and replicase. ORFs 2 to 6 would code for the viral envelope proteins, and ORF7 would code for the nucleocapsid protein. Viral replicase and polymerase are large-sized proteins, 260 and 163 kDa respectively, and both of them contain three possible glycosylation sites. Envelope proteins (ORFs 2 to 6) located at 3' end are small, between 30 and 19 kDa. All of them contain more than two possible glycosilation sites, especially ORF3 which contains 7 sites. All of these proteins contain hydrophobic sequences at the amino (N-) and carboxy (C-) terminal ends that might work as leader sequence and membrane anchor. Generally, they are hydrophobic proteins, in accordance with their location associated to a membrane. ORF6 should be pointed out, with 3 hydrophobic segments located within the 90 amino acid residues at the N-terminal end. On the other hand, the protein coded by ORF7, possibly corresponding to the viral nucleocapsid, is extremely basic with arginine, lysine and histidine residues at the N-terminal end. The amino acid sequences of LV and TV viral polymerase, structural proteins and nucleocapsid show an identity of between 29% and 67% in comparison with LDV virus, and between 20% and 36% in comparison with EAV virus. This suggests that the evolution of the PRRS virus is closer to LDV than to EAV.

The disease caused by PRRSV is responsible for severe losses to the pig industry. For this reason, vaccines capable of preventing the infection caused by PRRSV have been developed.

In general, the vaccines against known PRRSV, described in patent claims WO 92/21375, WO 93/06211, WO 93/07898 and ES P9301973 are vaccines obtained from viruses grown on macrophages and subsequently inactivated. Patent application ES P9301973 provides a vaccine capable of avoiding porcine reproductive and respiratory syndrome (PRRS). The vaccine has been demonstrated to be efficacious in avoiding reproductive alterations in sows, such as the farrowing of stillborn, mummified or living but weak piglets, repetition of estrus and similar problems produced by the virus causative of PRRS. Likewise, it has been verified that the vaccine induces cellular immunity in the vaccinated animals. The said vaccine contains a suitable quantity of PRRS viral antigen, Spanish strain (PRRS-Olot), inactivated, together with an adjuvant and preservative.

The present invention provides a second generation vaccine in which recombinant DNA technology has been employed with the objective of obtaining new vaccines capable of efficaciously protecting against the infection caused by PRRSV. The vaccines of this invention contain, at least, one recombinant PRRSV protein. On the other hand, the present invention provides new PRRSV diagnostic systems or kits that involve the use of enzymatic immunoassay techniques (ELISA) that use recombinant PRRSV proteins. These recombinant vaccines do not require manipulation of the complete virus, but rather of only part of it, eliminating the risk of an accident that would free virus, representing a considerable advantage over the present inactivated PRRSV vaccines.

The production of recombinant proteins by means of genetic engineering is a fact that has been described previously. Numerous expression and production systems of recombinant proteins are known. One of the most effective systems for large-scale production of recombinant proteins is based on the replication of recombinant baculoviruses derived from the *Autographa californica* nuclear polyhedrosis virus (AcNPV), in insect cells in culture. The description of the baculovirus expression technique is described in the following articles:

a) LucKow, V. A. & Summers, M. D., "Trends in the development of baculovirus expression vectors". Bio/Technology, 6:47–55, (1988); and b) Bishop, D. H. L., "Baculovirus expression vectors". Seminars in VIROLOGY, 3:253–264 (1992).

This invention provides recombinant PRRSV proteins, in particular of the PRRS-Olot isolate, produced in an expression system of baculoviruses multiplied on permissive host cell culture. The recombinant baculoviruses capable of producing such recombinant proteins, as well as the transfer vectors used, constitute additional objectives of the invention. The procedures for the obtainment of such recombinant baculoviruses and proteins is also an objective of this invention.

The invention provides also new vaccines for the vaccination of pigs for their protection against the infection caused by PRRSV, comprising, at least, one recombinant protein of those provided by this invention and an adequate carrier or adjuvant.

The invention provides also a diagnostic kit to detect the presence of antibodies that specifically recognize PRRSV in a biological sample from pigs (e.g.: blood, serum, sputum, saliva or milk). The kit comprises at least one recombinant protein of those provided by this invention and adequate detection methods.

The invention provides also a diagnostic kit for the detection of the presence of antigen (PPRSV) in a biological sample from pigs (e.g.: blood, serum, sputum, saliva, milk or tissue). The kit comprises at least one antibody which specifically recognizes PRRSV obtained by immunizing animals with, at least, one recombinant protein of those provided by this invention and adequate detection means.

BRIEF DESCRIPTION OF THE FIGURES

FIG. 1 shows the consecutive sequence of the 3383 bp cloned from the PRRS-Olot isolate.

FIG. 2A–F shows the amino acid sequence corresponding to the proteins coded by ORF2 (FIG. 2A), ORF3 (FIG. 2B), ORF4 (FIG. 2C), ORF5 (FIG. 2D), ORF6 (FIG. 2E) and ORF7 (FIG. 2F).

FIG. 9 shows the results of antigen titration by ELISA. In the figure reference is made to antigen titration (a), absorbance values read at 405 nm (b), and antigen dilutions [in units of $1/100$] (c).

DESCRIPTION OF THE INVENTION

Figure 3:
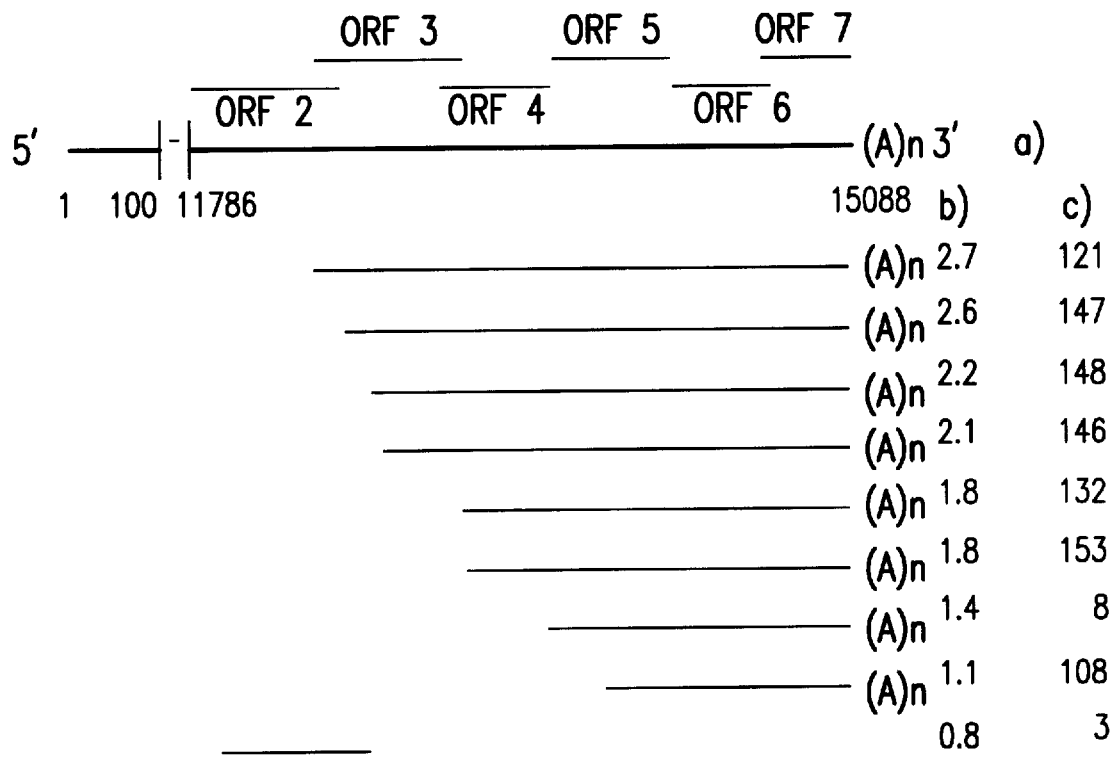
FIG. 3 shows the different extension of clones pPRRS-8, pPRRS-108, pPRRS-121, pPRRS-132, pPPRS-146, pPPRS-147, pPPRS-148, pPRRS-153 and pPRRS-3, in comparison with LV, as well as the ORFs contained in each one of them. In this figure, reference is made to the PRRSV genome (a), size in Kb (b) and number of the clone (c).

Our Laboratory has made a search for the PRRS causative agent in recent years. The main consequence of this has been the isolation of the virus denominated PRRS-CY-JPD-P5-6-91. It was deposited at the ECACC (with accession number V93070108 deposited on Jul. 1, 1993) and a vaccine was developed against PRRSV containing the inactivated virus (Patent Application ES P9301973).

Since then, our research efforts have addressed the isolation and cloning of the PRRSV (PRRS-CY-JPD-P5-6-91) genome, denominated as PRRS-Olot in this description, in order to enable the development of new recombinant vaccines effective against the infection caused by PRRSV. To that end, a genome segment of the said PRRS-Olot genome has been cloned. The cloned fragment corresponds to the 3' viral genome, and represents a consecutive sequence of 3338 bp. This segment contains the six open reading frames corresponding to ORFs 2 to 7 described for LV and TV. They code for the structural proteins of the virus (nucleocapsid and envelope) possibly involved in viral antigenicity and immunogenicity. The proteins coded by PRRS-Olot ORFs 2 to 7 are similar to the corresponding LV and TV proteins. Their characteristics are summarized in Table 1, where are indicated, in relation with each ORF, the relative positions of the nucleotides, the number of base pairs (bp), the number of amino acids (Aac), the molecular weight of each protein (in KDa) and the glycosylation sites.

TABLE 1

| Characteristics of the PRRS-Olot virus ORFS | | | | | |
|---|---|---|---|---|---|
| ORF | Nucleotides (site) | bp | Aac (No.) | Protein (KDa) | Glycosylation |
| 2 | 65–811 | 747 | 249 | 28.4 | 2 |
| 3 | 673–1467 | 795 | 265 | 30.8 | 7 |
| 4 | 1215–1763 | 549 | 183 | 20.0 | 5 |
| 5 | 1763–2362 | 600 | 200 | 22.4 | 2 |
| 6 | 2353–2871 | 519 | 173 | 19.0 | 2 |
| 7 | 2864–3247 | 384 | 128 | 13.8 | 1 |

FIG. 1, which accompanies this description, shows the complete consecutive sequence of the 3383 bp of the cloned fragment corresponding to the 3' end of the PRRS-Olot viral genome. This nucleotide sequence shows 95% homology in comparison with the corresponding sequences of the LV and TV isolates. These two last isolates show, among themselves, 99% homology. The changes in the nucleotide sequence of the PRRS-Olot isolate are found along the entire sequence, but are concentrated especially in 5' end. We should point out, in comparison with LV, the deletion of three nucleotides at position 1860 of PRRS-Olot.

FIG. 2 (2A–2F) of this description shows the amino acid sequences of the proteins coded by ORFs 2 to 7 of the PRRS-Olot virus. At protein level, 99% homology is observed between PRRS-Olot and LV ORF7, as expected for a nucleocapsid viral protein and therefore the more conserved. The percentage of homology for the rest of the proteins ranges between 93% for ORFs 3, 4 and 5 reaching a value of 96.5% for ORFs 2 and 6. All of them present glycosylation sites similar to those described for LV except for ORF4 of the PRRS-Olot virus, which has an extra glycosylation site. With regards to the above-mentioned changes in the PRRS-Olot protein amino acids, 50% of the changes are into chemically similar amino acids, whereas the rest of the changes are into different amino acids. As mentioned for LV, excepting ORF7, the rest of the proteins present a high degree of hydrophobicity, possibly in accordance with their association to membranes since they are viral envelope proteins.

Recombinant proteins corresponding to the expression of PRRS-Olot ORFs 2 to 7 can be produced in a suitable expression system and, advantageously, in an expression system of recombinant baculoviruses multiplied in permissive host cell culture. The global procedure for the obtainment of these recombinant proteins basically comprises the following general stages:

I. Preparation of the cDNA sequence to be inserted into a baculovirus; and

II. Obtainment of recombinant baculoviruses expressing the recombinant proteins.

These general stages are in turn subdivided into other sub-stages. This way, the preparation of the cDNA sequence to be inserted comprises the sub-stages of:

I.a Isolation and purification of the PRRS-Olot virus;

I.b Isolation of the viral RNA of the PRRS-Olot virus; and

I.c Synthesizing of the cDNA from the PRRS-Olot genomic RNA.

On the other hand, the obtainment of recombinant baculoviruses expressing the recombinant proteins corresponding to PRRS-Olot ORFs 2 to 7, comprises the sub-stages of:

II.a Preparation of the PRRS-Olot ORF gene to be inserted;

II.b Inserting of the said gene into a baculovirus transfer vector;

II.c Transfection of permissive host cells with the said transfer vector which has the corresponding PRRS-Olot ORF gene inserted.

II.d Selection of the recombinant baculoviruses expressing the recombinant protein corresponding to the inerted ORF.

The characterization of the recombinant baculoviruses and the analysis and purification of the recombinant proteins are then carried out.

All these stages are described in detail further down in this description.

The procedure employed for the obtainment of the recombinant proteins provided by this invention begins with the isolation and purification of the PRRSV, specifically PRRS-Olot, in accordance with the protocol described in Example 1. Once the PRRS-Olot had been isolated and purified, the viral RNA was isolated and for that purpose a commercial kit (Pharmacia) was used, which makes use of a method based on the selection and purification of the viral RNA containing a poly(A) sequence at 3' end (Example 2). The obtained RNA was analyzed in neutral agarose gels at 0.7% by staining with ethidium bromide, and only one band of material with molecular weight of between 5000 and 23000 bp was observed.

Afterwards, the cDNA corresponding to the 3' end viral RNA was synthesized (Example 3) with a commercial kit (Boehringer), by means of a strategy which takes advantage of the presence of a poly(A) tail, and uses an oligo d(T) as extension primer capable of being extended with reverse transcriptase enzyme and synthesizing cDNA molecules. To clone the 3' upstream RNA regions, an oligonucleotide annealing to a specific viral genome sequence located approximately at 2500 bp from 3' end was used. A second synthesis was carried out using an oligonucleotide of 20 nucleotides instead of the oligo $d(T)_{12}$ (Example 3.1). cDNA synthesis was verified and quantitated by means of counting the radioactivity incorporated in the synthesized material and electrophoresis in alkaline and neutral agarose gels. After this, the cloning and sequencing of the cDNA were carried out (Example 3.2). To this end, the first thing done was a size selection of synthesized cDNA fragments of between 1000 and 5000 nt (nucleotides). The purified cDNA was cloned in blunt ends in pMTL25 vector. The analysis of the PRRSV-positive clones was done by means of plasmid DNA preparations and mapping of the restriction sites, based on the LV sequence. Only 9 out of the 300 analyzed plasmids were positive and contained inserts of between 800 and 2600 bp. The definitive verification of the authenticity of these cDNA clones was done by their direct sequencing, using the dideoxy method applied to double-stranded plasmids.

The majority of the obtained positive PRRS clones contained a common poly(A) end and different 5' ends. The clones were denominated as pPRRS-8, pPRRS-108, pPRRS-121, pPRRS-132, pPRRS-146, pPRRS-147, pPRRS-148 and pPRRS-153. Clone pPRRS-3 was extracted from the second synthesis. To obtain the recombinant baculoviruses expressing the genes of the proteins coded by PRRSV-Olot ORFs 2 to 7, the following procedure was generally and separately followed: First, the gene from each ORF to be inserted was prepared, except the ORF3 gene which did not require previous preparation. For the preparation of these genes and depending on each particular case, the pMTL25, pMTL24 and pMTL22 plasmids were used before they were transferred into baculovirus transfer vectors. The genes corresponding to ORFs 2 to 7 were obtained from the clones that had been obtained previously. After successive manipulations, they originated new recombinant plasmids. The recombinant plasmids, which contained the genes corresponding to each ORF inserted, were purified following the alkaline lysis technique and were characterized by mapping with restriction endonucleases and sequencing of the insertion regions. The new vectors obtained were denominated as pPRRS-ORFN, where N stands for the number of each ORF (N=2 to 7).

Then, each ORF gene was cloned into a suitable transfer vector. The transfer vector used was pAcYM1 (Matsuura et al., J. Gen Virol. 68, 1233–50). After successive manipulations, new recombinant plasmids, each one of them containing the inserted ORF gene, were originated. The recombinant plasmids obtained were purified following the alkaline lysis technique and characterized by mapping with restriction endonucleases. The insert ends were sequenced in order to verify correct insert region sequence. The new transfer vectors obtained were analyzed to verify that the inserted genes had the correct orientation for their expression by the AcNPV virus polyhedrin promoter. The transfer vectors obtained were:

| Denomination | ORF |
|---|---|
| pRRRS-Bac8 | 2 |
| pPRRS-Bac2 | 3 |
| pPRRS-Bac9 | 4 |
| pPRRS-Bac3 | 5 |
| pPRRS-Bac5 | 6 |
| pPRRS-Bac7 | 7 |

*Spodoptera frugiperda* cells, Sf 9 clone, were then transfected with mixtures of purified infectious DNA of the AcRP23-lacZ parenteral virus and the corresponding transfer vector. Once this transfection had been done, the recombinant baculoviruses were identified by plaque color phenotype assay after the staining of the viral progeny with X-gal, and then purified.

The recombinant baculoviruses obtained were deposited at the European Collection of Animal Cell Cultures (ECACC), Porton Down, Salisbury, Whiltshire SP4 OJG (U.K.).

Examples 4 to 9 describe in detail the obtainment of recombinant baculoviruses expressing the genes coded by ORFs 2 to 7, respectively.

The PRRS-Olot ORF 2 to 7 recombinant proteins can be used for diagnosis purposes to detect the presence of specific PRRSV antibodies (Example 12), and to detect the presence of antigen (PRRSV) by means of antibodies that specifically identify the PRRSV obtained by immunization of animals with, at least, one recombiant protein corresponding to one of PRRS-Olot ORFs 2 to 7. Additionally, these proteins can also be used to immunize animals against PRRSV. Therefore, the said proteins can be used to formulate recombinant vaccines capable of effectively protecting swine against infection caused by PRRSV. These vaccines may be active or passive. Active vaccines can be prepared by suspending at least one of the recombinant proteins provided by this invention in an immunologically acceptable diluent and an adjuvant. A passive vaccine can be obtained by immunizing animals with the said proteins and isolating the polyclonal antibodies against the said proteins. After antibody isolation and purification, they can be used in vaccine applications. In a specific embodiment of this invention, recombinant vaccines are obtained capable of effectively protecting from the infection caused by PRRSV, comprising the viral antigen (antigenic phase) together with an immunologically acceptable diluent and an adjuvant.

For the preparation of the antigenic phase, insect cells—preferentially *Spodoptera frugiperda* cells—were infected with the diverse recombinant baculoviruses capable of producing the recombinant proteins corresponding to the PRRSV ORFs 2 to 7, and incubated under conditions suitable for the expression of the said proteins. Immediately afterwards, the cells were collected, washed, resuspended in suitable buffer, and then used in the preparation of the aforesaid recombinant vaccines.

In a specific embodiment, the antigenic phase is composed of a homogenate of insect cells infected with recombinant baculoviruses expressing a single recombinant PRRSV protein, such as, preferably, ORF3, ORF5 and ORF7 (Example 13). In another specific embodiment, the antigenic phase is composed of a homogenate of a mixture of insect cells infected with different recombinant baculoviruses expressing, each one of them, a different recombinant PRRSV protein, such as a mixture of insect cells infected with the recombinant baculoviruses expressing, for example, the proteins corresponding to ORF3, ORF5 and ORF7.

In general, vaccines were formulated containing as antigenic phase an amount of about $50 \times 10^6$ insect cells infected with baculoviruses expressing the recombinant protein in question. When the vaccine contains diverse recombinant proteins, the antigenic phase is composed of a quantity of about $50 \times 10^6$ insect cells infected with baculoviruses per the recombinant protein in question, i.e., for a formulation of a vaccine containing the proteins corresponding to ORFs 3, 5 and 7, the antigenic phase is composed of about $50 \times 10^6$ insect cells infected with baculoviruses expressing the ORF3 recombinant protein, $50 \times 10^6$ insect cells infected with baculoviruses expressing the ORF5 recombinant protein, and $50 \times 10^6$ insect cells infected with baculoviruses expressing the recombinant ORF7 protein (Example 13).

Phosphate-buffered saline solutions (PBS) or other similar saline solutions may be used as immunologically acceptable diluents.

As adjuvant, in general, any of the adjuvants habitually used to formulate vaccines may be used, either aqueous—such as aluminum hydroxide, alumina gel suspensions, QuilA—or others, like oily adjuvants, based on mineral oils, glycerides and oleic ether-acid derivatives. In particular, it has been confirmed that an oily adjuvant composed of a mixture of Marcol® 52, Simulsol° 5100 and Montanide® 888, gives very good results. Marcol® 52 is a low density mineral oil manufactured by ESSO Española S.A., Simulsol® 5100 is a polyethoxy oleate ether commercialized by SEPIC, and Montanide® 888 is a high purity anhydromannitol octadecenoate ether commercialized by SEPIC.

The vaccines of this invention can also contain cell response potentiator (CRP) substances, i.e., substances that potentiate helper T cell subpopulations ($Th_1$ and $Th_2$) such as IL-1 (interleukin-1), IL-2, IL-4, IL-5, IL-6, IL-12, g-IFN (gamma interferon), cell necrosis factor and similar substances which could, in theory, provoke cell immunity in vaccinated animals. These CRP substances could be used in vaccine formulations with aqueous as well as oily adjuvants.

Likewise, other types of adjuvants that modulate and immunostimulate cell response can be used, such as MDP (muramyl dipeptide), ISCOM (Immuno Stimulant Complex) or liposomes.

The vaccines of this invention may be obtained by suspending or mixing the antigenic phase with the immunologically acceptable diluent and the adjuvant. When the adjuvant is oily an emulsion is formed which—in a specific and preferred case—if the adjuvant is a mixture of Marcol 52, Simulsol 5100 and Montanide 888 the vaccine will be a double water/oil/water emulsion, type w/o/w.

In the case that the vaccine will contain CRP substances, these substances may be added both to the antigenic phase and to the adjuvant. Alternatively, if the vaccine does not contain any CRP substances, these can be injected, if so desired, simultaneously in a separate site different from the site of inoculation.

Additionally, these vaccines can contain combinations of different porcine pathogens containing, besides one recombinant PRRSV protein or more, one or more of the pathogens mentioned below, allowing for the preparation of polyvalent vaccines. Among these pathogens, but not limited exclusively to them, are *Actinobacillus pleuropneumoniae, Haemophilus parasuis, Porcine parvovirus, Leptospira, Escherichia coli, Erysipelothrix rhusiopathiae, Pasteurella multocida, Bordetella bronchiseptica, Porcine respiratory coronavirus*, Rotavirus or against the pathogens causative of Aujeszky's disease, swine influenza and transmissible gastoenteritis.

Safety and efficacy trials with the vaccines of the present invention have evidenced that the said vaccines are safe and at the same time efficacious.

It has been possible to confirm that one dose of 2 ml of a quantity of viral antigen or antigenic phase equal to or higher than $50 \times 10^6$ infected insect cells expressing one or more of the recombinant PRRSV proteins, administered via deep intramuscular route followed by a revaccination with a dose of 2 ml of vaccine, can effectively protect vaccinated animals from the infection caused by PRRSV. Likewise, it has been possible to verify that some of the vaccines object of the trial—those identified as rPRRS C and rPRRS D—are capable of inducing cellular immunity in vaccinated animals, based on the fact that sows vaccinated and revaccinated with the said vaccines did not present serological at the moment of challenge and, nevertheless, they were protected (Example 14, Tables 4 and 10).

With the purpose of determining and evaluating the efficacy of the prepared recombinant vaccines in the prevention of PRRS in pregnant sows, a trial was designed consisting of the vaccination of pregnant sows with the different vaccines and then submitting them to a discharge test with virulent virus. Based on the obtained results, it has been possible to evaluate the efficacy of the vaccines objective of this trial. In order to evaluate the efficacy of these vaccines, the reproductive results, the number both of piglets alive and dead at different stages of the piglets' life period, as well as the analysis of the serological results in sows and piglets were taken into account (Example 14).

DETAILED DESCRIPTION OF THE INVENTION (EXAMPLES)

Example 1

Obtainment and Purification of the PRRS-Olot Virus.

1.1—Obtainment of pig's lung aleveolar macrophages 1.1.1—Animals. 7 to 8 week old pigs, a cross between Belgium Landrace and Large White breeds, were used. The animals, from our own farms, were seronegative to the following diseases: Aujeszky's, porcine parvovirosis, foot-and-mouth, classic swine fever, swine influenza (types H1N1 and H3N2) and transmissible gastroenteritis.

1.1.2—Isolation of macrophages. The animals were anesthetized by injecting in the jugular vein 0.1 g of sodium thiopental per each 10 kg body weight. Then, they were sacrificed and the lungs extracted, after ligating the trachea below the epiglotis and sectioning above the ligation. The extracted lung was washed externally with PBS. Successive internal washings were done (4 to 5) with a total of 500 ml of PBS supplemented with antibiotics at 1:500 (PEG solution: 1000 IU/ml penicillin, 1 mg/ml streptomycin, and 0.5 mg/ml gentamicin), in order to obtain macrophages. These washings were collected together and centrifuged at 300 g for 15 minutes. The following step was to wash the cells twice with PBS by means of consecutive centrifugation/sedimentation, to finally resuspend in DMEMs medium (DMEM supplemented with non-essential amino acids at 10033, GIBCO), containing sodium pyruvate 1 mM, and antibiotics (1:1000 of PEG).

The cells were counted by staining with trypan blue in Newbauer chamber. 0.1 ml of $10^{-1}$ macrophage suspension was added to 0.4 ml of DMEMs and 0.5 ml of trypan blue solution. In the majority of cases the number of cells obtained ranged between 1 and $1.2 \times 10^9$.

Sterility controls were carried out on the macrophage cells by means of seedings in culture media suitable for the detection of bacteria and fungi. Absence of mycoplasma was verified by cytochemical detection with DAPI (4',6-diamidino-2-phenylindole) which selectively attaches to the DNA and forms high specificity DNA-DAPI fluorescent complexes.

1.2—Replication of the virus in pig alveolar macrophages. Cell culture vials (150 cm$^2$) were used, containing 100 ml of a macrophage suspension ($3 \times 10^6$ cells/ml) in the DMEMs medium described above, except for the addition of fetal calf serum (FCS) at 5%. The cells were infected with PRRS-Olot virus, isolated by Laboratorios Sobrino and denominated PRRS-JPD-P5-6-91 (ECACC, accession number V93070108). Infection was done at $10^{-3}$ infection multiplicity, and the infected cells were incubated at 37° C. for 24 h. After this period had elapsed, the medium was withdrawn and substituted by fresh DMEMs containing 2% FCS and antibiotics; incubation was continued at 37° C.

The cultures were observed periodically with microscope to determine the cytopathic effect (CPE) produced by the virus on the macrophages. Generally, CPE by 3–4 days of infection was 70–80%. Giant deformed cells appeared. Normally, the titre of these preparations was $10^{6.55}$ TCID$_{50}$/ml (tissue culture infectious dose 50 per milliliter). Macrophages infected at $10^{-4}$ multiplicity produced viral yields of one order of magnitude less.

The presence of virus in these cells was determined by the immunoperoxidase in monolayer assay on pig macrophage cells obtained as described in Example 1 (1.1.2). Briefly, this was done the following way: In 96-well titration plaques, 100 µl of macrophages were infected ith 50 µl of PRRS-OlOT virus replicated on macrophages. The plaques were incubated for 48 hours at 37° C. Once incubation had been completed, the medium was withdrawn and the plaques washed two times with saline solution (0.1M NaCl). Subsequently, they were fixed with 20% formaldehyde after consecutive incubations at 37° C., −30° C. and formaldehyde at 20%. After washing twice with saline solution, 50 µl of a 1:50 dilution of an anti-PRRS serum from a challenged animal. Simultaneous incubations were done with a negative serum from an uninfected animal. Incubation was for 1 hour at 37° C. After withdrawal of the previous solution, they were washed two times with saline solution. Immediately, 0.1 µg of Protein A (Sigma) in 50 µl was added and incubated at 37° C. for 1 hour. The assay was developed with AEC (3-amino-9-ethyl-carbazole) dissolved in dimethylformamide in the presence of acetate buffer and oxygenated water. After 15–30 minutes at room temperature in darkness, the plates were observed by microscope. Infected cells appeared stained dark red, in comparison with uninfected cells which were colorless.

1.3—PRRS virus purification. The virus was purified from PRRSV-infected cell cultures. The culture was clarified by means of centrifugation (20 minutes, 6500 g). The supernatant was concentrated 10× by using a Millipore-Minitan ultrafiltration system (4.5 pSi, 300 kDa pore-size filter). Then, the virus was sedimented by means of centrifugation (5 h, 20000 g). The supernatant was discarded and the precipitate solubilized with PBS containing 1 mM phenylmethylsulfonyl fluoride (PMSF) (Sigma) at 4° C., overnight. The virus was purified in discontinuous sucrose gradient (20–50% w/v in PBS) by means of centrifugation at 95000 g for 3 h. Once the centrifugation had been completed, the band containing the virus was extracted from the gradient, diluted with Tris/EDTA buffer and finally centrifuged overnight at 26000 g for virus sedimentation.

The purified virus was analyzed by means of electrophoresis in polyacrilamide-SDS gels at 12% (Laemmli, U.K., Nature, 227:680, 1970). Total protein was detected by staining with coomassie blue, and immunoblots (Towbin, H., Staehelin, T., and Gordon, J., 1979. Proc. Natl. Acad. Sci. USA, 76: 4350–4354). The blots were developed with peroxidase-Protein A (Sigma) conjugate using a covalescent anti-PRRSV serum. It was not possible to observe any specific band related with PRRSV in coomassie-stained gels because of contamination with proteins from the macrophages. However, several viral proteins of molecular weights between 15.5 and 30 KDa were identified by immunoblot. With longer developing times, it was also possible to observe bands of molecular weights over 60 KDa but as these were also detected in uninfected macrophages, it was concluded that they were not PRRS virus-related proteins.

Example 2

Isolation of the Viral RNA

A commercial Pharmacia P-L Biochemicals kit was used. The method is based on the selection and purification of the viral RNA containing a 3' end poly(A) tail. The viral capsid rupture was done with guanidinium chloride purification of RNA-poly(A) with an oligo-celullose (dT) matrix.

Briefly, the isolation of the PRRS-Olot virus RNA was carried out the following way: The purified virus sedimented by overnight centrifugation at 40000 g. Afterwards, the supernatant was discarded and the precipitate solubilized with 0.4 ml of the kit extraction buffer. After adsorption into the cellulose-d(T) matrix, and consecutive washings with the low and high salt concentration buffers, the RNA-poly (A) was eluted with high ClNa concentration. The RNA was precipitated by adding 1:10 volume of 2.5M potassium acetate, 0.25 mg/ml glycongen and 2 volumes of ethanol (>2 h. at −20° C.). Once this period had elapsed, the RNA was recuperated by centrifugation at 16000 g for 30 minutes. After washing the precipitate with ethanol at 75%, it was resuspendend in 20 $\mu$l of TE buffer (10 mM Tris-ClH pH=8.0 and 1 mM EDTA).

The obtained RNA was analyzed in 0.7% neutral agarose gels by staining with ethidium bromide. A single band of material within 5000 and 23000 bp molecular weight was observed. The absence of low molecular weight material must be pointed out and therefore the possibility of cellular DNA or RNA. However, the amount of material obtained was low—not higher than 100 ng of RNA/250 ml of macrophage culture infected with the virus. This low yield agrees with the low yield of purified virus, as shown by electrophoresis in polyacrilamide gels and electron microscopy (data not shown).

Example 3 cDNA Synthesis from the PRRS-Olot Virus Genomic RNA 3.1—Preparation of the cDNA. The cDNA corresponding to the 3' end RNA of the PRRS-Olot viral isolate was synthesized. The strategy takes advantage of the presence of a poly(A) tail in order to use the oligo d(T) as extension primer that can be extended with reverse transcriptase and can synthetize DNA molecule copies. To clone the RNA regions previous to the 3' end, an oligonucleotide with specific sequence of the viral genome located at approximately 2500 bp of the 3' end was used. cDNA synthesis was carried out using a commercial kit (Boehringer). The procedure, in brief, was: 0.1 $\mu$g of PRRS RNA-poly(A), obtained as described in the previous example, was incubated in the presence of 1 mM each dNTPs (dATP, dCTP [5–10 $\mu$Ci of $^{32}$P-$\alpha$-dCTP], dGTP and dTTP), 25 units of an RNase inhibitor, 0.8 $\mu$g oligo d(T)$_{12}$, and 40 units of reverse transcriptase in 20 $\mu$l final volume. The reaction was incubated at 42° C. for 1 h and then the synthesis of the second strand was started in the same tube. To that end, buffer, RNasa, and 25 units of *E. coli* DNA polymerase were added. Incubation was for 1 hour at 22° C., and 10 minutes at 65° C. Finally, to generate blunt ends, 4 units of DNA T4 polymerase were added. After 10 minutes at 37° C., reaction was stopped by adding EDTA and sarkosyl. A second cDNA synthesis was done under the same conditions, except for the fact that 5' CGGGCTCGAGCCTTTGGCGA3' [SEQ ID NO:8] oligonucleotide was used instead of oligo d(T)$_{12}$. In both cases, the mixture was extracted with phenol:chloroform and the material was precipitated with ethanol, as described in the previous example.

cDNA synthesis was checked and quantified by means of counting the radioactivity incorporated in the synthesized material, and electrophoresis in alkaline and neutral agarose gels.

3.2—Cloning and sequencing. First, the synthesized cDNA was size selected to avoid the cloning of excessively small segments. For that purpose, the material from the cDNA synthesis was recovered by centrifugation (30 minutes, 16000 g) . The precipitate was vacuum dried, dissolved with Tris/EDTA buffer (TE) pH=8.0, and loaded in 1% agarose gel. The cDNA fragments between 1000 and 5000 bp were recovered from the gel with DEAE-cellulose paper and from the latter by elution with ClNa and subsequent precipitation. Purified cDNA was cloned in blunt ends in the pMTL25 vector, a vector derived from the pUC18. With that purpose, the vector was linearized with SmaI and treated with alkaline phosphatase to reduce the vector background. After ligation with DNA T4 ligase, *E. coli* XL-1Blue competent cells were transformed with the ligation mixture in the presence of X-gal (5-bromo-4-chloro-3-indolyl β-D-galactopyranoside) (Boehringer) and IPTG (Isopropyl β-D-thiogalactopyranoside) (Gold Bioch), which allows the initial selection of recombinant colonies by color (blue colonies without insert in comparison with white ones with insert).

The analysis of the positive PRRS clones was done by means of plasmid DNA preparations (Birnboim & Doly, Nucleic Acids Res., 7, 1513–1523, 1979), and mapping of restriction sites based on LV sequence. Only 9 out of the 300 plasmids analyzed were positive and contained inserts between 800 and 2600 bp. The definitive verification of the authenticity of these cDNA clones was done by their direct sequencing, using the dideoxy chain-termination method applied to double-strand DNA (Sanger, F., et al., J. Mol. Biol., 94:441–448, 1975). The universal oligonucleotides (5'GTAAAACGACGGCCAGT3') and [SEQ ID NO:9]

reverse (5'AACAGCTATGACCATG3') oligonucleotides [SEQ ID NO:10] were used to sequence all the clones. The majority of the obtained PRRS clones contained one common poly(A) tail and different 5' ends. The clones were denominated pPRRS-8, pPRRS-108, pPRRS-121, pPRRS-132, pPRRS-146, pPRRS-147, pPRRS-148 y pPRRS-153. From the second cDNA synthesis, clone PRRS-3 was obtained. FIG. 3 shows the different extension of these clones in comparison with LV, as well as the ORFs contained in each one. On the other hand, FIG. 1 shows the consecutive sequence of the 3383 bp cloned from the PRRS-Olot isolate, and FIG. 2 (2A–2F) shows the amino acid sequences corresponding to the proteins coded by each ORF.

Example 4
Obtainment of Recombinant Baculoviruses Expressing the Protein Gene Coded by ORF2

4.1—Preparation of the ORF2 gene

Figure 4:
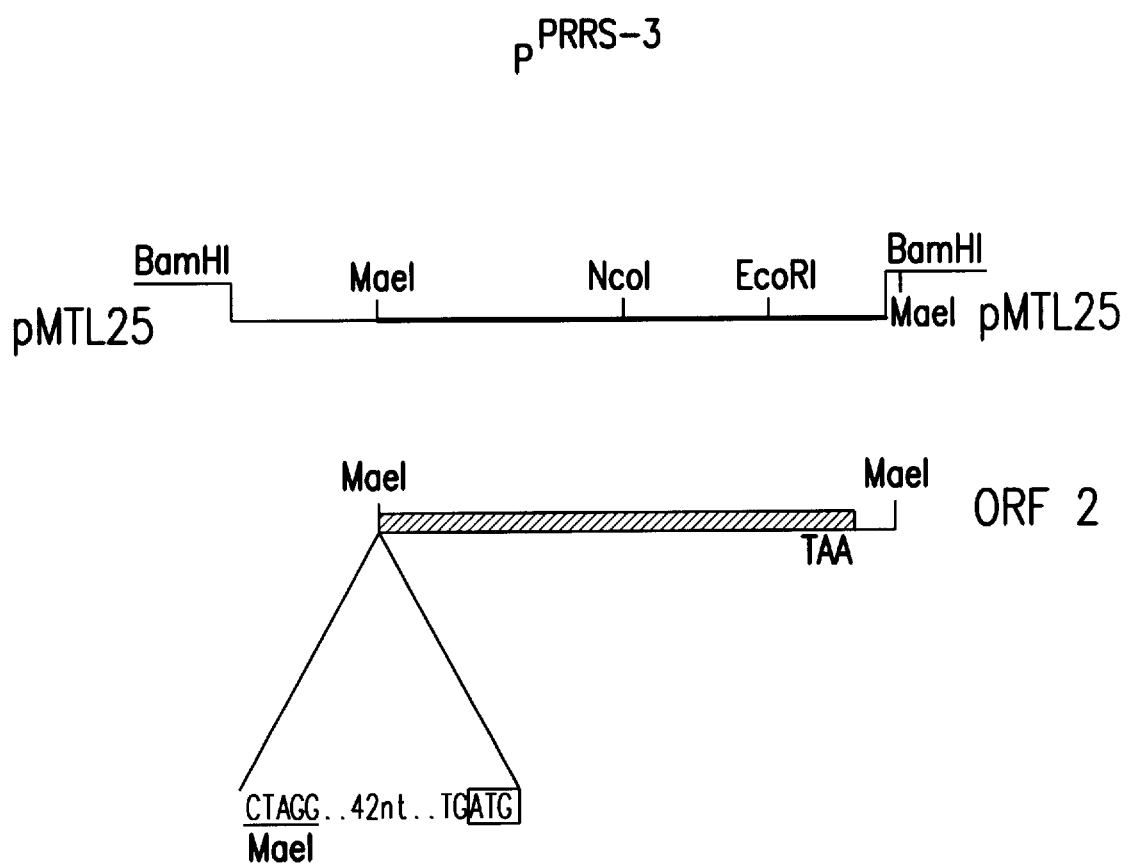
FIG. 4 shows pPRRS-3 clone containing the gene of the protein coded by ORF2.

The pMTL25, pMTL24 y pMTL22 genes, derived from the pUC18 vector, were used for the preparation of the different ORFs mentioned in this description, before they were cloned in baculovirus transfer vectors. The vector used is indicated for each particular case. The ORF2 gene is 747 bp in size, and was obtained from cDNA pPRRS-3 clone (FIG. 4). The DNA was digested with MaeI, and the insert of approximately 900 bp was purified in agarose gel. The cohesive insert ends were transformed into blunt ends by means of treatment with the Klenow fragment of the E. coli DNA polymerase. Cloning was done in the pMTL25 treated with SmaI, alkaline phosphatase and purified in 1% low melting agarose gel. After ligation with DNA T4 ligase (Boehringer), E. coli XL-1Blue cells were transformed with the ligation mixture and the positive clones selected initially by color. The recombinant plasmids containing the inserted ORF2 gene were purified according to the alkaline lysis method (Birnboim & Doly, Nucleic Acids Res., 7, 1513–1523, 1979), and characterized by mapping with restriction endonucleases and sequencing of the insertion regions.

The newly obtained vector was denominated pPRRS-ORF2. In it, the ORF2 initiation codon (ATG) is located approximately at 50 bp from the beginning of the insert and the BamHI site.

4.2.—Insertion of the ORF2 gene into a baculovirus transfer vector

The baculovirus transfer vector used in all the experiment described in this patent was pAcYM1 vector (Matsuura et al., J. Gen Virol. 68, 1233–50), which has a single BamHI insertion site.

The vector was donated by Professor D. H. L. Bishop (I.V.E.M., Oxford, United Kingdom). For the insertion, the vector was thoroughly digested with the BamHI endonuclease and then treated with the alkaline phosphatase enzyme to avoid vector religation. ORF2 codes for a 28.4 KDa protein. Briefly, the insertion of the corresponding gene into the pAcYM1 vector used pPRRS-ORF2 plasmid as a starting material. In this plasmid, the ORF2 gene is flanked by two BamHI sites. Thus, the pPRRS-ORF2 is digested with BamHI and loaded in 1% low melting agarose gel in order to obtain the 935 bp fragment. This fragment was inserted into the BamHI site of pAcYM1 according to Struhl's method (Biotechniques 6, 452–453, 1985), using the DNA T4 ligase (Boehringer) to ligate the insert the vector. The ligation mixture was used to transform E. coli DH5 cells. The obtained recombinant plasmids containing the inserted ORF2 gene were purified according to the alkaline lysis method (Birnboin & Doly, supra), characterized by mapping with restriction endonucleases and sequenced the insert edges to corroborate the correct sequence of the insertion regions. The newly obtained transfer vector was denominated pPRRS-Bac8 and it was shown to have the PRRS gene in the correct orientation for its expression by the AcNPV baculovirus polyhedrin promoter.

4.3—Transfection and selection of baculoviruses

Spodoptera frugiperda cells, Sf 9 clone, were cotransfected with a mixture of purified infective DNA of parental virus AcRP23-lacZ (500 ng), donated by Dr. Posee (I.V.E.M., Oxford, U.K.) and the transfer vector pPRRS-Bac8 DNA (2 μg). The parental virus DNA was linearized with the Bsu36I enzyme within the lacZ gene (Kitts et al., Nuc. Acids Res. 18, 5667–72.1990) in order to increase the efficiency of the recombination. For cotransfection, the lipofectin (Gibco-BRL) method was used (Felgner et al., Proc. Natl. Acad. Sci. U.S.A., 84, 7413–7417, (1987)). After cotransfection, the cells were incubated for 5 days in complete TNMFH medium supplemented with 5% fetal calf serum (FCS) and antibiotics, until cytopathic effect was observed.

Then, the transfection supernatant was recovered and the recombinant viruses identified by plaque assay. The AcRP23-lacZ parental virus shows blue lysis plaques in the presence of X-gal substrate because the β-galactosidase gene is being expressed. Recombinant viruses were initially identified by the clear plaques after staining the viral progeny with X-gal. A number of plaques of each virus were picked and subjected to three purification rounds, before a high titre virus stock was prepared. The recombinant baculovirus finally obtained was denominated AcNPV, PRRS 2. It has been deposited at the European Collection of Animal Cell Cultures (ECACC) with accession number V94021007.

Example 5
Obtainment of Recombinant Baculoviruses Expressing the Protein Gene Coded by ORF3

5.1—Insertion of ORF3 gene into a baculovirus transfer vector

Figure 5:
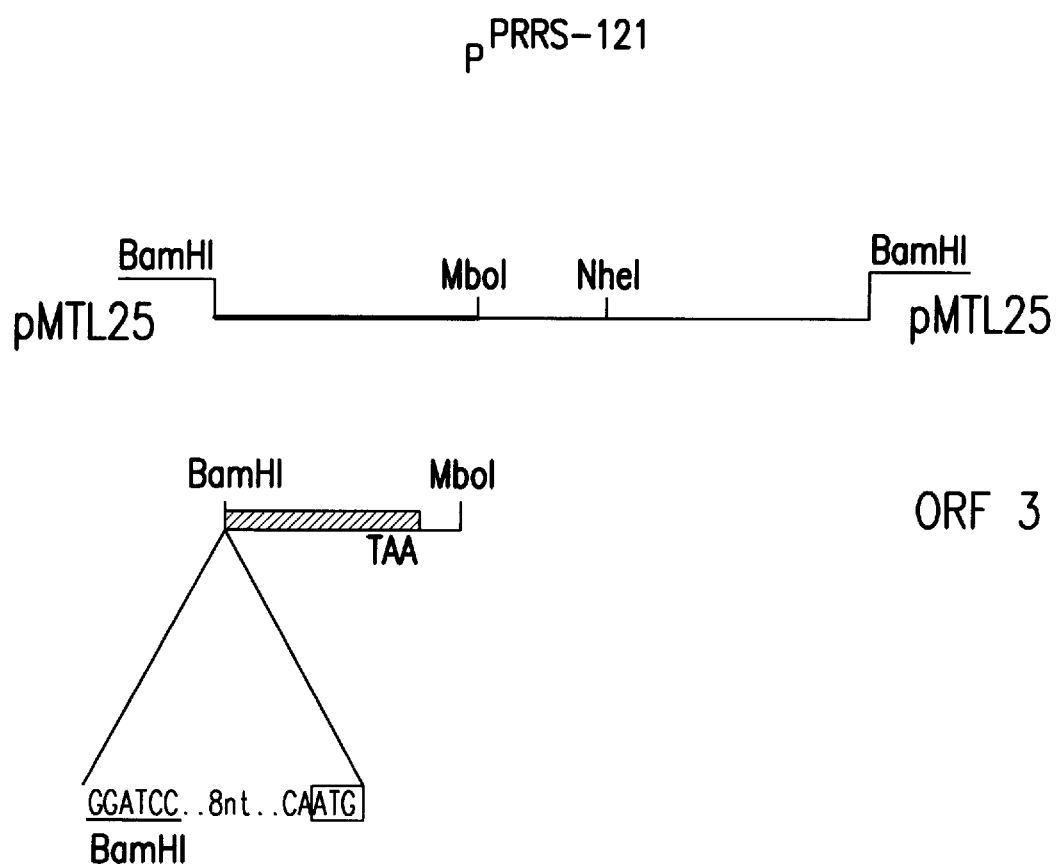
FIG. 5 shows pPRRS-121 clone containing the gene of the protein coded by ORF3.

ORF3 codes for a protein of an estimated molecular weight of 30.8 KDa. pPRRS-121 plasmid DNA was used as a starting material for the insertion of the corresponding gene in the pAcYM1 transfer vector (FIG. 5). In this vector, the ORF3 initiation codon is located 10 bp from the BamHI site. The gene can be excised by double digestion with the BamHI and Sau3A enzymes, which generates cohesive ends compatible with BamHI. After digestion, the mixture was loaded in 1% low melting agarose gel, and a 1009 bp fragment was purified. It was isolated and then ligated to the pAcYM1 vector treated with BamHI and alkaline phosphatase, using the T4 ligase DNA enzyme. Subsequently, E. coli DH5 cells were transformed and the recombinant plasmids purified and characterized according to the procedures described above. Once the correct sequence and insert orientation towards the polyhedrin promoter had been verified, the new transfer vector was denominated pPRRS-Bac2.

5.2—Transfection and selection of recombinant baculoviruses

The procedure used for the transfection and selection of recombinant baculoviruses was similar to the one described above for ORF2 (Example 4.3). The recombinant baculovirus obtained was denominated AcNPV, PRRS 3. It has been deposited at ECACC with accession number V94011325.

Example 6
Obtainment of Recombinant Baculoviruses Expressing the Protein Gene Coded by ORF4

6.1—Preparation of the ORF4 gene

Figure 6:
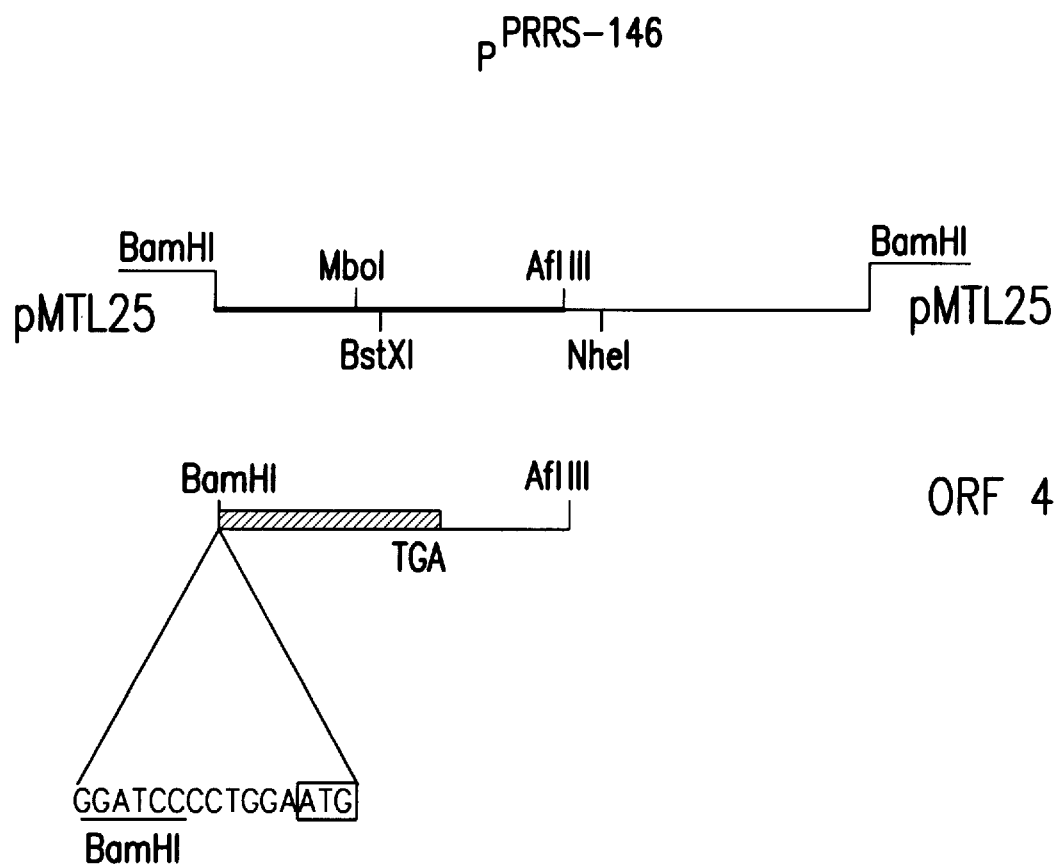
FIG. 6 shows pPRRS-146 clone containing the gene of the protein coded by ORF4.

The size of the ORF4 gene is 549 bp. It was obtained from the pPRRS-146 clone (FIG. 6) digested with the BamHI, AflIII and PstI enzymes. The first two enzymes flank the insert and PstI was used to cleave a vector DNA fragment, of similar size to the ORF4 gene which would have made gene isolation difficult. A 1112 bp fragment was purified in low melting agarose gel and cloned in pMTL22 vector digested with BamHI and NcoI (compatible with AflIII). After ligation with T4 ligase DNA and transformation of E. coli DH5 cells, the recombinant plasmids were purified accoding to the alkaline lysis method (Birmboin & Doly, supra), and characterized by restriction endonuclease mapping. The newly obtained vector was called pPRRS-ORF4. It contains the ORF4 initiation ATG codon located 5 bp from the BamHI site.

6.2—Insertion of the ORF4 gene in a baculovirus transfer vector

ORF4 codes for a 20.0 KDa protein. The corresponding gene was obtained from the pPRRS-ORF4 plasmid by digestion with BamHI plus BglII. The 1112 bp fragment was purified in 1% low melting agarose gel and directly cloned in pAcYMI-BamHI. The procedures for the identification and characterization of the recombinant clones were identical to those described above (Example 4.2). Once the correct orientation and insert sequence had been verified, the new plasmid was denominated pPRRS-Bac9. This plasmid was used for posterior transfection experiments and preparation of recombinant baculoviruses.

6.3—Transfection and selection of recombinant baculoviruses

The procedure followed for the transfection and selection of recombinant baculoviruses was similar to the procedure described above for ORF2 (Example 4.3). The recombinant baculovirus was denominated AcNPV, PRRS4. It has been deposited at ECACC with accession number V94021008.

Example 7
Obtainment of Recombinant Baculoviruses Expressing the Protein Gene Coded by ORF5

7.1—Preparation of the ORF5 gene

Figure 7:
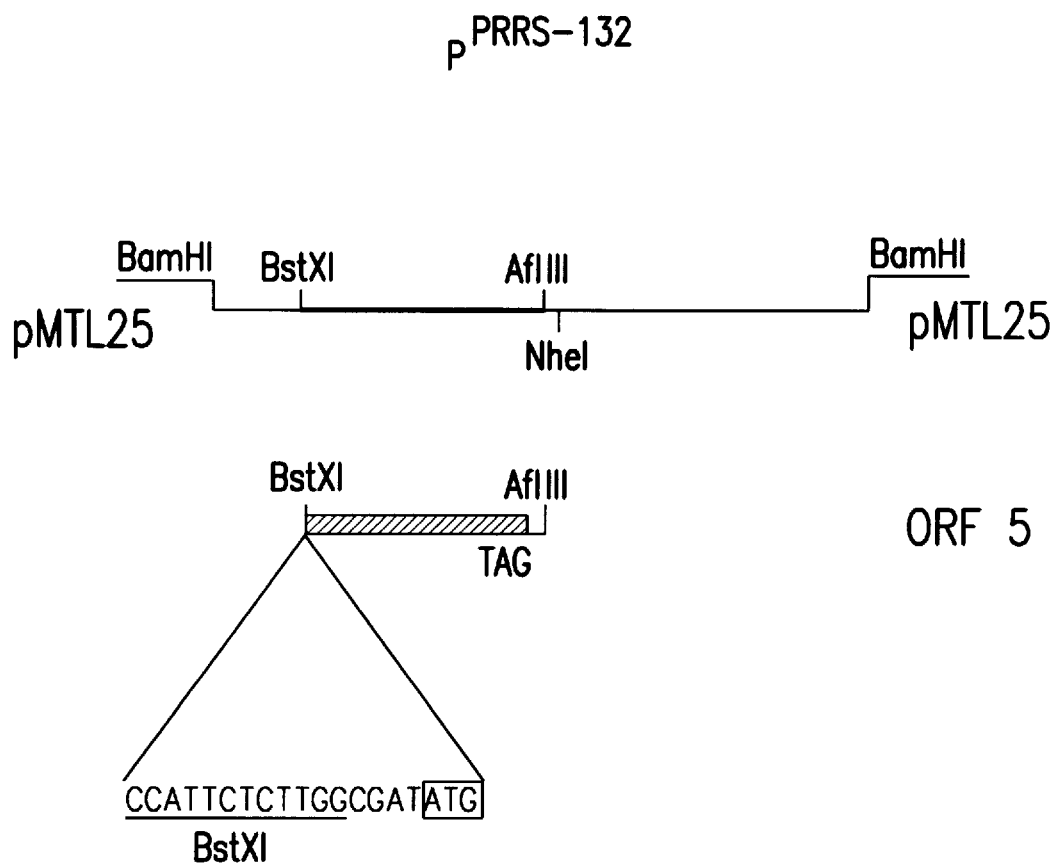
FIG. 7 shows pPRRS-132 clone containing the gene of the protein coded by ORF5.

The size of ORF5 is 600 bp. It was obtained from clone pPRRS-132 (FIG. 7). The DNA was digested with the BstXI and BfrI enzymes, and a 700 bp fragment containing ORF5 was purified in 1% low melting agarose gel. After converting the fragment ends from cohesive to blunt by means of treatment with T4 polymerase DNA, the fragment was cloned in the pMTL25/SmaI vector. The method used was similar to the procedures described in Example 4.1. The newly obtained vector was denominated pPRRS-ORF5. It contains the ORF5 initiation ATG codon, located 15 bp from the beginning of the gene.

7.2—Insertion of the ORF5 gene in a baculovirus transfer vector

ORF5 codes for a 22.4 KDa protein. To insert the corresponding gene in the transfer vector, the pPRRS-ORF5 vector was digested with enzyme BamHI. The 706 bp fragment was purified in 1% low melting agarose gel and ligated directly to the pAcYml-BamHI transfer vector. The recombinant plasmids were characterized as described above. The new transfer vector was denominated pPRRS-Bac3. It was used in subsequent transfection experiments.

7.3—Transfection and selection of recombinant baculoviruses

The procedure followed for the transfection and selection of recombinant baculoviruses was similar to the procedure described above for ORF2 (Example 4.3). The recombinant baculovirus obtained was denominated ACNPV, PRRS5 and has been deposited at ECACC with accession number V94011326.

Example 8
—Obtainment of Recombinant Baculoviruses Expressing the Protein Gene Coded by ORF6

8.1—Preparation of the ORF6 gene

Figure 8:
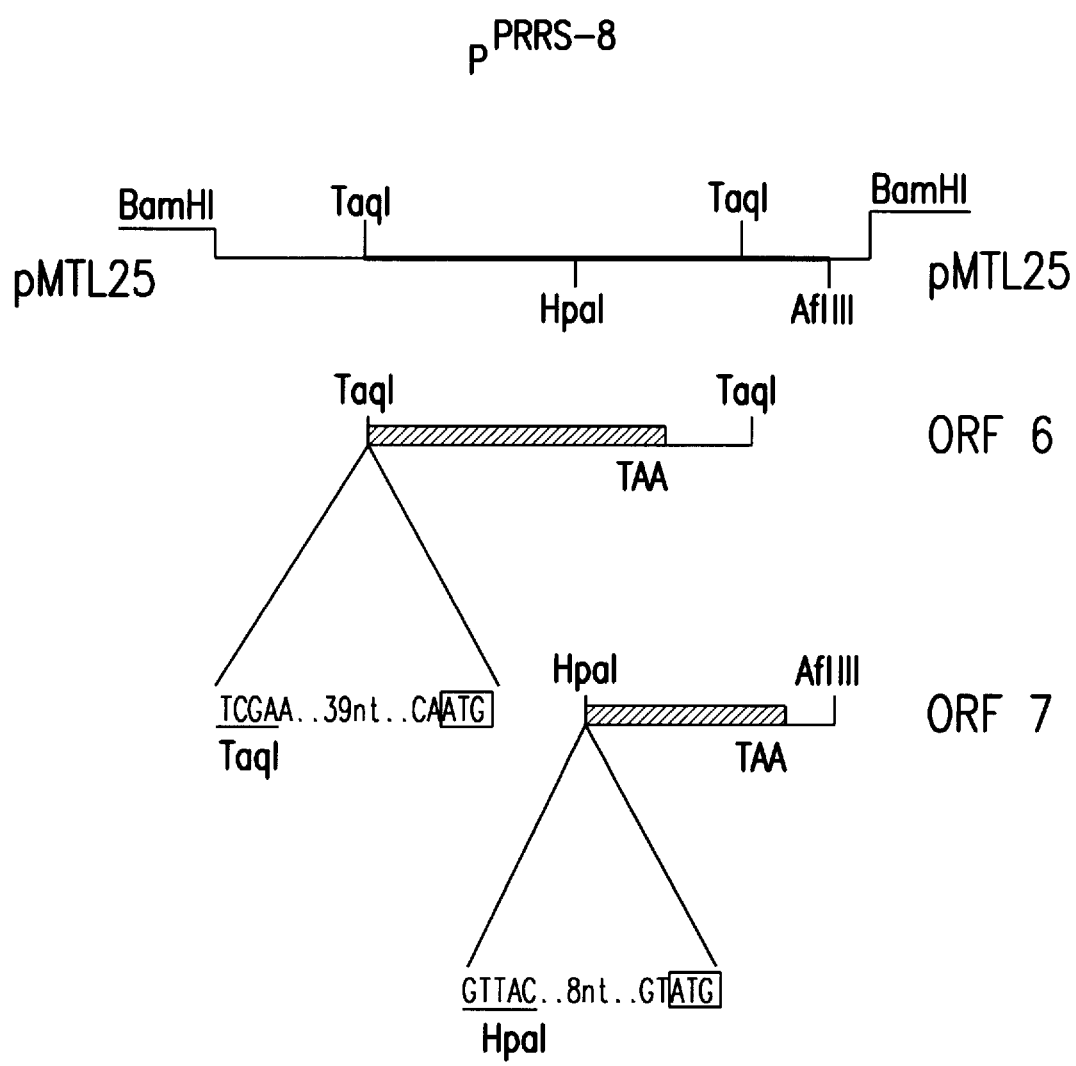
FIG. 8 shows pPRRS-8 clone containing the genes of the proteins coded by ORF6 and ORF7.

The size of the ORF6 gene is 519 bp. It was prepared from the pPRRS-8 gene clone (FIG. 8). First, the DNA was digested with the AflIII enzyme, which allowed the elimination of bands approximate in size to the ORF6 gene. A 990 bp AflIII—AflIII fragment was purified in 1% low melting agarose gel and digested with TaqI. The new 790 bp fragment was purified in low melting agarose gel and cloned in the pMTL24 vector treated with AccI and alkaline phosphatase. Subsequently, the steps described in Example 4.1 were done. The new vector was denominated pPRRS-ORF6. It contains the ORF6 initiation codon located at 46 bp from the beginning of the gene.

8.2—Insertion of the ORF6 gene in a baculovirus transfer vector

ORF6 codes for a 19.0 KDa protein. This is supposed to be the envelope protein and, on account of its hydrophobic nature, it is considered to be a membrane-spanning protein. For the insertion of the corresponding gene in the transfer vector, the pPRRS-ORF6 vector, containing the ORF6 gene cloned at pMTL24 AccI site, was digested with the BamHI enzyme. The 790 bp fragment was purified from the 1% agarose gel and ligated directly to vector pAcYM1-BamHI. The new transfer vector was denominated pPRRS-Bac5. It was used in subsequent transfection experiments.

8.3—Transfection and selection of recombinant baculoviruses

The method used for the transfection and selection of recombinant viruses was similar to the procedure described above for ORF2 (Example 4.3). The recombinant baculovirus obtained was denominated ACNPV, PRRS6. It has been deposited at the ECACC with accession number V94011327.

Example 9
—Obtainment of Recombinant Baculoviruses Expressing the Protein Gene Coded by ORF7

9.1—Preparation of the ORF7 gene

The size of the ORF7 gene is 384 bp. It was prepared from the pPRRS-8 gene clone (FIG. 8). Fragment AflIII—AflIII described in Example 8.1 was digested with the HpaI enzyme. The 430 bp AflIII-HpaI fragment containing the ORF7 gene was purified in low melting agarose gel and subsequently cloned in the pPMTL25 vector digested with NcoI-SmaI. The analysis and characterization of recombinant colonies was done as described in Example 4.1. The new vector was denominated pPRRS-ORF7. It contains the ORF7 initiation codon located at 16 bp from the beginning of the gene.

9.2—Insertion of the ORF7 gene in a baculovirus transfer vector

ORF7 codes for a 13.8 KDa protein. This is supposed to be the viral nucleoprotein. For the insertion of the corresponding gene in the transfer vector, the pPRRS-ORF7 plasmid was digested with the BglII and BamHI enzymes. The resulting 430 bp fragment was isolated from a low melting agarose gel and ligated directly within the pAcYM1-BamHI vector. After the suitable characterizations, the new pPRRS-Bac7 transfer vector was obtained. It was used in subsequent transfection experiments.

9.3—Transfection and selection of recombinant baculoviruses

The method used for the transfection and selection of recombinant baculoviruses was similar to the procedure described above for ORF2 (Example 4.3). The recombinant baculovirus obtained was denominated AcNPV, PRRS7. It has been deposited at the ECACC with accession number V94011328.

Example 10
Analysis of Recombinant Proteins and Immunodetection

Sf9 cells were infected with different recombinant baculoviruses at multiplicity of infection of 1 PFU/cell and incubated at 27° C. until the cultures were harvested. Different cell cultures were done in monolayer and in suspension. In all the cases, results were similar. The cultures were harvested at different post-infection times. The optimal harvesting time for each recombinant virus was determined. This ranged from between 48 and 96 p.i.h. (post-infection hours). The cells were harvested by centrifugation at 1500 rpm for 10 min, washed twice with PBS pH:7.4 and subsequently resuspend and lysed with 25mM bicarbonate solution. They were centrifuged at 10000 rpm for 10 minutes and the soluble cytoplasmic fraction was separated from the remaining insoluble cell debris. The total cell extracts as well as the different fractions were analyzed by electrophoresis in 11% polyacrilamide gels and stained with coomassie blue or transferred to nitrocellulose membranes for immunological detection. Bands were observed by staining with coomassie blue with molecular weights of 28.4, 30.8, 20.0, 22.4, 19.0 and 13.8 KDa. These sizes correspond respectively to the sizes expected for the genes coded by ORFs 2, 3, 4, 5, 6 and 7. There is a significant variation in the expression levels of the different genes: ORFs 3, 5 and 7 at considerable level, ORFs 2 and 4 at appreciable level and ORF6 at low level. The gene's lower expression levels, corresponding to ORFs 2 and 6, might be due to the larger distance, 42 and 39 nucleotides respectively, between the protein initiation ATG codon and the polyhedrin baculovirus promoter. On several occasions, it has been demonstrated that this distance should essentially be maintained at a minimum in order to obtain a good expression. Another factor, responsible for low expression, could be the high hydrophobic nature of these proteins.

When analyzing separately the soluble and insoluble fractions of the infected cells, it has been observed that, except for ORF7, most of the expressed PRRS proteins are insoluble and remain associated to the membrane debris. This may be due to the hydrophobic and glycosylated nature of these proteins. The majority of these glycoproteins contain transmembrane regions that anchor them to the membranes. Such characteristics make the purification of these proteins from cell extracts difficult.

For immunodetection, the proteins were transferred to nitrocellulose membranes, according to standard methods (Burnette, Anal. Biochem. 112, 195–203, 1981; Towbin et al., Proc. Natl. Acad. Sci. U.S.A. 76, 4350–4354, 1979). Protein transfer was done in a semi-dry device (Bio-Rad) at 22 V for 30 minutes. Then, the nitrocellulose strips were blocked with 3% powder skim milk in Tris-HCl 20 mM pH 7.5, NaCl 500 mM (TBS) for 1 hour at room temperature. Subsequently, the strips were incubated first for two hours at room temperature with an anti-PRRS pig antiserum (C-45) diluted 1/100 in TBS-0.05% Tween 20, washed with TBS-0.05% Tween 20 for 30 minutes at room temperature, and then incubated with anti-pig IgG conjugated to alkaline phosphatase (dilution 1/1000) (Sigma) for 1 hour. The strips were washed once more and, finally, developed with an NBT (nitro blue tetrazolium) (Sigma) and BCIP (5-bromo-4-chloro-3-indolyl-phosphate) (Sigma) solution in NaCl 100 mM, $MgCl_2$ 5 mM, diethanolamine 100 mM, pH: 9.5, until the appearance of visible bands. The reaction was stopped with distilled water. In all the cases in which specific reactions were seen by immunoblot, proteins of molecular weight equivalent to the estimated ORF sizes were obtained. In some cases, specifically in ORFs 3 and 5, the presence of other larger-sized bands, till 45 KDa, were observed. These bands would represent different protein glycosylation forms, in agreement with the foreseen potential sites.

10.1—Antigenic characterization of the recombinant proteins

The correct antigenicity of the recombinant proteins expressed in baculovirus was checked by their reaction to different animal sera in an immunoblotting assay. Recombinant proteins expressed and transferred to nitrocellulose according to the above method, were made to react with a collection of previously characterized swine sera containing anti-PRRSV antibodies. The sera had been obtained in animals infected experimentally (#1–4) or naturally (#5–8).

Proteins corresponding to ORFs 3, 5 and 7 were the first to be checked. Results are shown in Table 2.

TABLE 2

| Reactivity of sera from infected animals against ORF3, ORF5 and ORF7 recombinant proteins | | | |
|---|---|---|---|
| Serum no. | ORF3 | ORF5 | ORF7 |
| 1 | + | + | − |
| 2 | + | + | − |
| 3 | + | + | + |
| 4 | ND | + | + |
| 5 | ND | + | + |
| 6 | + | + | + |
| 7 | ND | + | − |
| 8 | ND | + | + |

+: Positive
−: Negative
ND: Not determined

This assay demonstrated that recombinant proteins 3, 5 and 7 are antigenically similar to native viral proteins 3, 5 and 7, respectively.

When the assay was done with recombinant proteins 2, 4 and 6, the results were of a greater variability than generally accepted in field sera. The reasons for this variability may be their low expression level and/or their high hydrophobicity.

These assays demonstrate that PRRSV recombinant proteins expressed in baculovirus system are not antigenicallly distinguishable from native viral proteins.

Example 11
Purification of the Recombinant Proteins

The strategy designed for recombinant protein purification should take into consideration the structural characteristics of the proteins. Two of these characteristics should be pointed out: (1) hydrophobic nature which makes them insoluble, and (2) presence of a large number of transmembrane regions which gives them a great affinity to membranes. In most cases, these characteristics do not make protein extraction and purification convenient, e.g.: for their use as a vaccine, when complete infected cells can be used, as described by different authors (Hall S. L., et al., Vaccine, 9, 659–667, Sept. (1991); Tordo N., et al., Virology, 194, 5269 (1993)). In spite of this, some attempts have been made to purify these proteins using ORF3 protein as a model.

11.1—Purification of the protein derived from ORF3

Sf9 cells were infected with the recombinant AcNPV, PRRS3 virus, according to the method described in the previous Example. The infected cells were collected by centrifugation at 400 g for 10 min, washed with PBS and resuspended at $20 \times 10^6$ cells/ml in PBS. The cells were disrupted by freezing/thawing and the soluble fraction was separated from the insoluble fraction by centrifugation. In all the cases, the insoluble fraction was used for the subsequent treatments.

Below is a description of some of the methods used:

Treatment with chaotropic agents

The insoluble fraction was first washed with 1M NaCl and then with 2M or 4M guanidinium chloride. The cell pellets were resuspended in the different buffers and maintained at room temperature for 1 hour. Then, the preparation was centrifuged at 15000 rpm for 5 minutes The presence of the recombinant protein in the different fractions was analyzed by elecrophoresis in 15% polyacrylamide-SDS gels (sodium dodecyl sodium sulfate).

The results obtained indicate that the sequential treatment with these salts yields a protein of 30% to 50% purity. This purified protein has been shown to be antigenically analogous to native protein, as it is recognizable by sera from infected animals, determined either by immunoblotting or indirect ELISA.

Treatment with detergents

Detergents at the following concentrations were used:

| | |
|---|---|
| NP40 | 0.5% |
| Octylglucoside | 2% |
| SDS | 0.5%, 1% and 2% |
| Sodium deoxycholate | 0.5%, 1% and 2% |

In all cases the cell preparations were done analogous to the one described above. Cell debris containing recombinant protein were treated with the above detergent concentrations and under the described conditions. In general, it can be stated that under these conditions, treatment with the different detergents did not enable the solubilization of a significant amount of recombinant protein. Only 0.5% SDS yielded protein of 50% estimated purity, although with very low yield. Antigenically, this protein reacts with infected animal sera by direct ELISA, although the efficacy is lower than what is obtained with the protein purified with chaotropic agents. To summarize, these partially purified proteins could be used in anti-PRRSV vaccines.

Example 12

Diagnostic Use

One of the main applications of the recombinant proteins provided by this invention is their use in the preparation of kits for the diagnosis of PRRSV field infections.

12.1—Preparation of antigen expressed in Sf9 for application in diagnosis.

Sf9 cells grown in monolayer or in suspension were infected at multiplicity of infection of 0.5 to 1 with the respective recombinant baculoviruses. Depending on which recombinant virus was used, cultures were harvested between 48 and 72 hours post infection. They were centrifuged at 400 g at 15° C. for 10 minutes and washed with PBS.

Finally, the cell pellets containing the recombinant proteins were resuspended in PBS with 2% octylglucoside (Sigma) and were allowed to stand on ice for 1 hour. They were then centrifuged at 1000 g for 10 minutes to eliminate cell debris. The supernatants were exhaustively dialyzed against PBS to remove the detergent, centrifuged at 10000 g for 30 minutes to remove precipitates and stored at −70° C. until later use.

12.2—ELISA for diagnosis.

Figure 9:
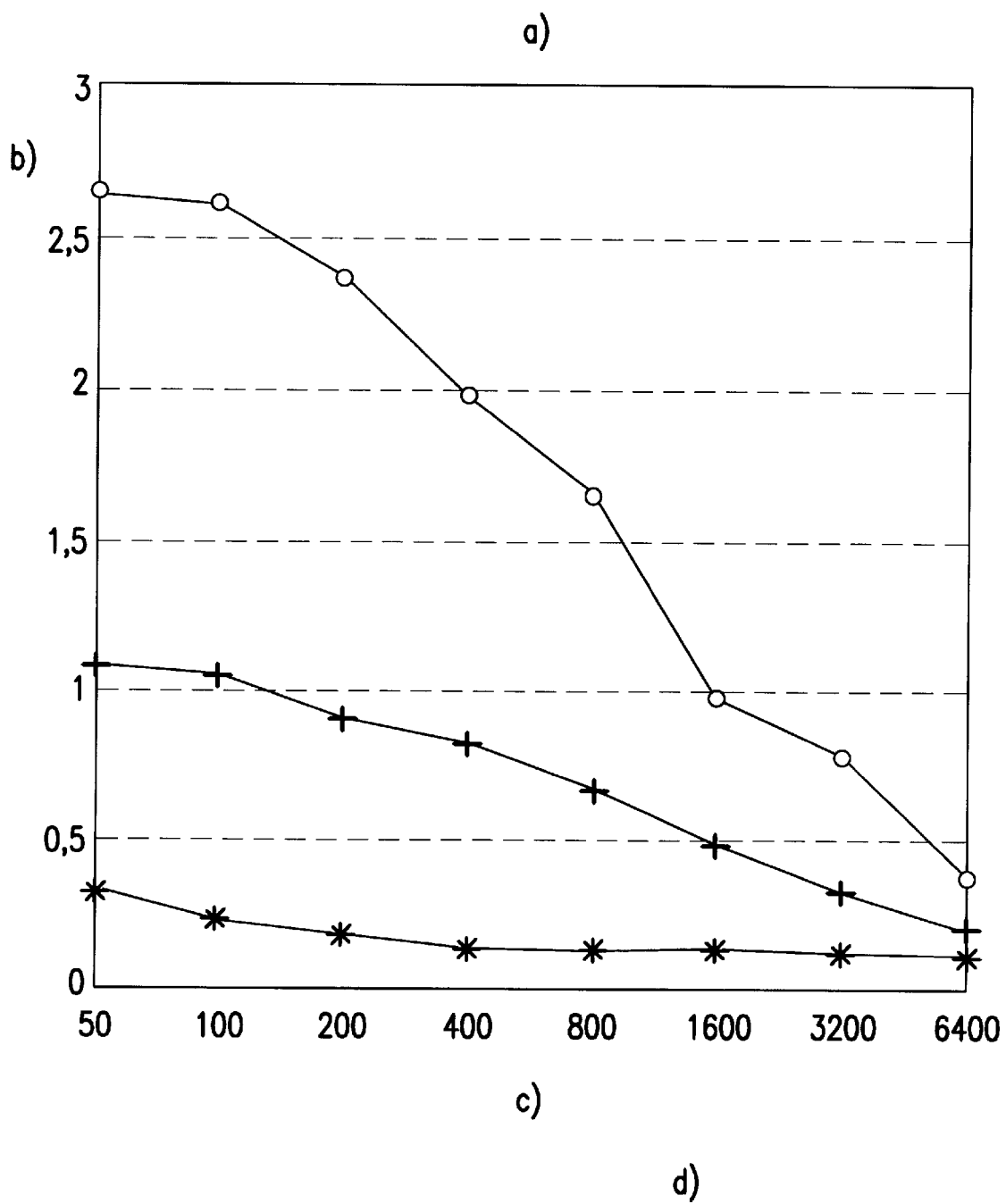
FIG. 9 shows the results from antigen titration by ELISA (absorbance monitored at 405 nm).

Polystyrene 96-well ELISA immuno plates (Polisorp, NUNC) were coated with different dilutions of the recombinant extracts mixture (ORF2, ORF3, ORF4, ORF5, ORF6 and ORF7), made in 50 mM carbonate buffer pH:9.6 (100 μl/well) by overnight incubation at 4° C. As shown in FIG. 9, the optimal dilution chosen for the plate coatings was 1/100. The plates were saturated with blocking buffer (1% skim milk in PBS) for 30 minutes at room temperature. Subsequently, were added different dilutions of the anti-PRRSV antisera made in blocking buffer. Incubation was continued for 1 hour at 37° C. After washing with PBS containing 0.05% Tween 20, peroxidase-labeled protein A (1/5000 dilution) was added, incubating at 37° C. for 1 hour. A washing like the previous one was done and the reaction was developed at room temperature for 10 minutes using ABTS [2,2'-azino-bis(3-ethylbenzthiazoline-6 sulfonic acid)] as substrate. The reaction was stopped with 1% SDS and absorbance was monitored at 405 nm.

Figure 10:
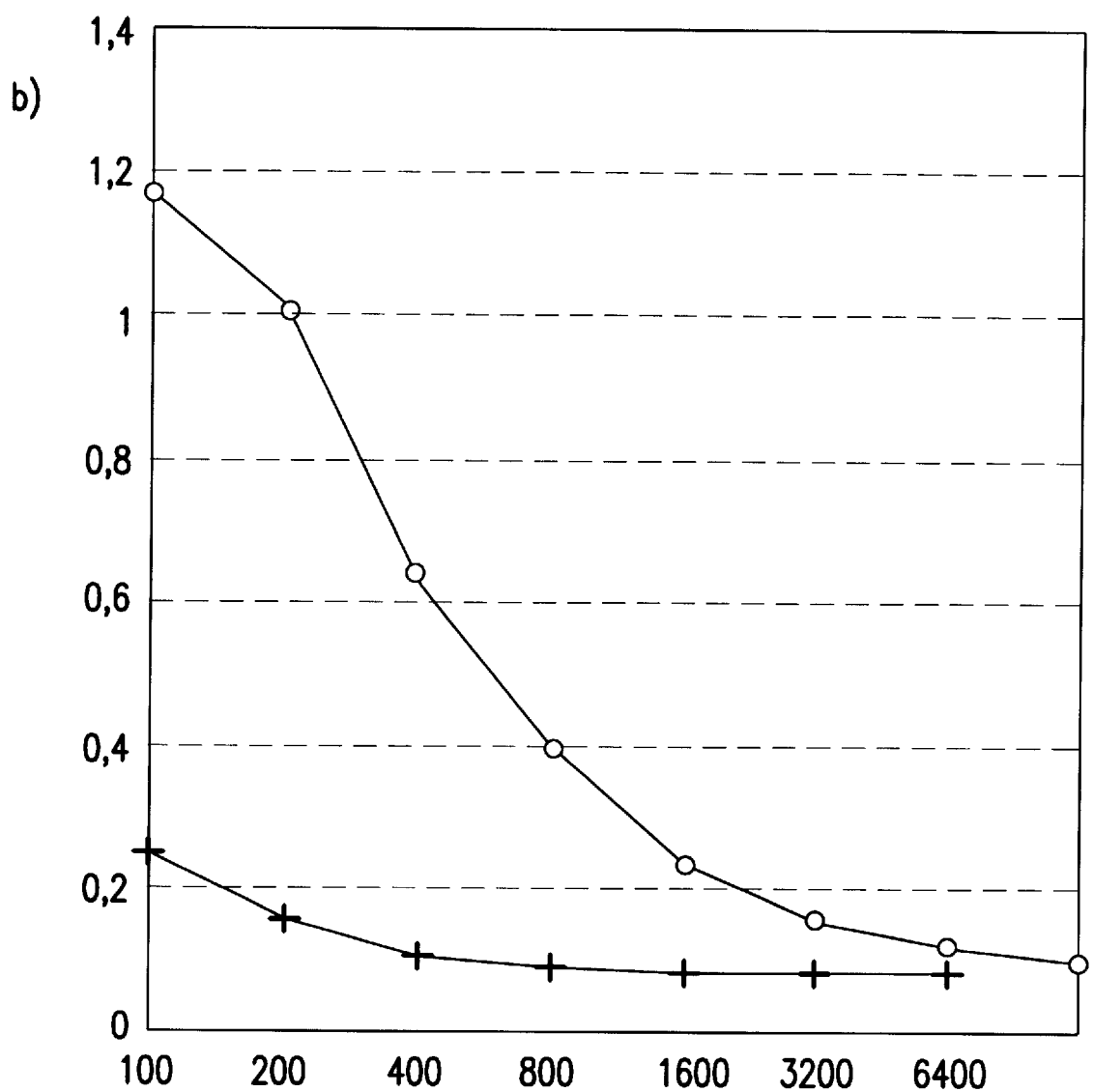
FIG. 10 shows the results from the titration, by ELISA, of a PRRS field serum obtained in an infected animal. The figure makes reference to the titration of the serum (a), absorbance values read at 405 nm (b), and serum dilutions [in units of $1/100-1/800$] (c).
Figure 11:
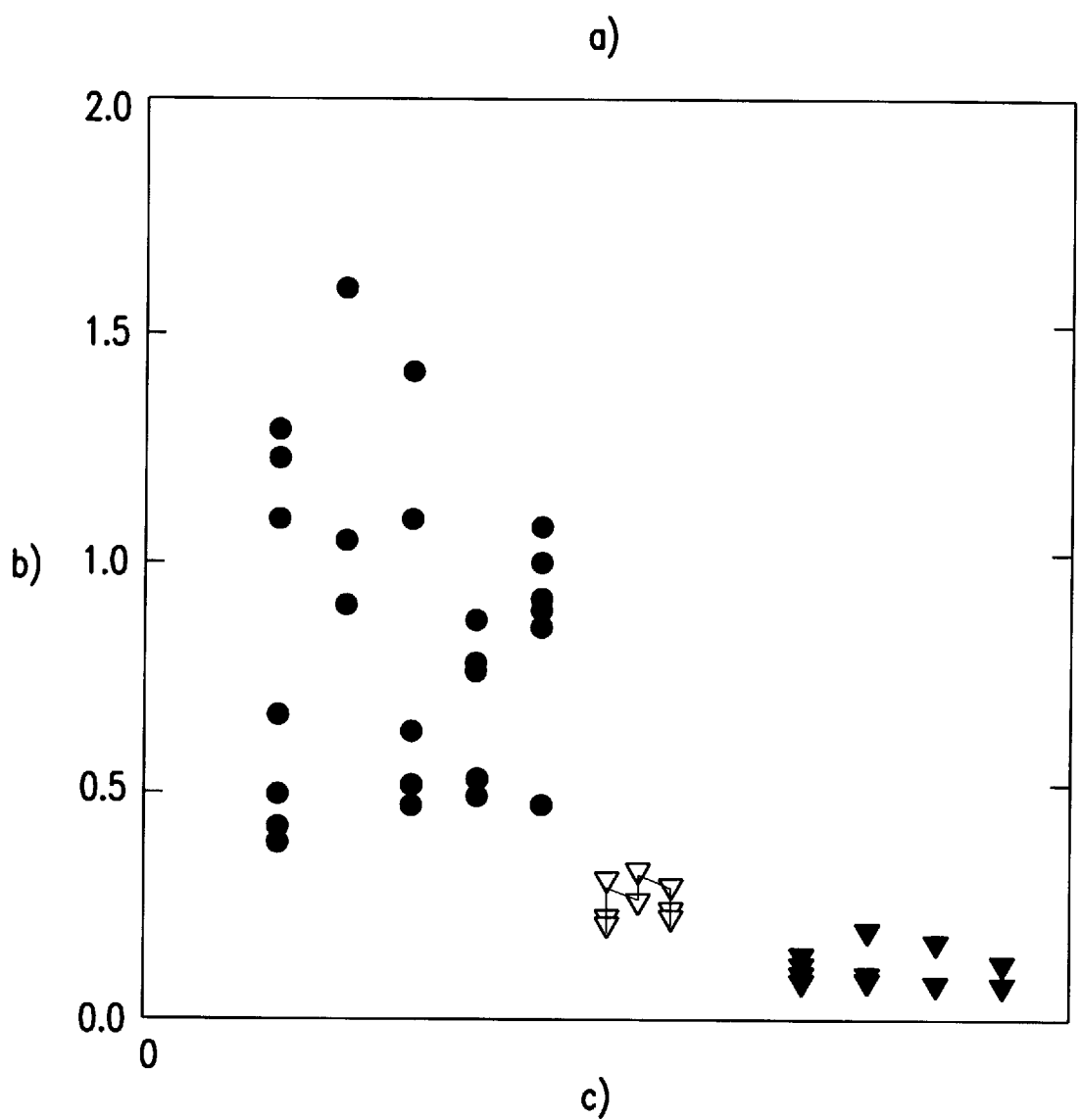
FIG. 11 shows the results obtained from a sampling experiment with several dozen field sera. The figure makes reference to the titration of the sera (a), absorbance values read at 405 nm (b), and the sera (c)

Usual ELISA titration results from an infected animal field serum are shown on FIG. 10. Field sera titrations normally range from 1/100 to 1/800 dilutions. The results obtained in a sampling experiment with several dozen field sera are shown on FIG. 11. It can be seen that titres obtained for clearly positive sera range from 0.4 to 1.7. Titres from uncertain sera range from 0.2 to 0.3. Negative sera give titres under 0.1. Thus, the conclusion arrived at is: the use of these recombinant proteins expressed in baculovirus is a safe, reliable and reproducible method, which enables to conclusively differentiate infected from uninfected animals.

Example 13

Formulation of the Recombinant Vaccines.

Diverse vaccines were prepared containing different recombinant PRRSV proteins, specifically PRRS-Olot [ECACC V93070108] in emulsion form, in accordance with the method described below.

*Spodoptera frugiperda* cells, clone Sf9 -hereunder Sf9- were infected at the rate of $1 \times 10^6$ cells/ml with the recombinant baculoviruses:

AcNPV, PRRS3, [ECACC V94011325];

AcNPV, PRRS5, [ECACC V94011326]; and

AcNPV, PRRS7, [ECACC V94011328], capable of producing, respectively, the recombinant proteins corresponding to ORF3, ORF5 and ORF7 of the aforesaid PRRSV (FIGS. 2, 4 and 6), at infection multiplicity of 0.1 plaque forming units (PFU)/cell. They were incubated at 27° C., with stirring at 100 rpm and 30% of $pO_2$, for 72 hours, in a 2 liter Braun-MD fermentor. Then the infected insect cells were collected by centrifuging at 1000 rpm for 10 minutes, washed with phosphate buffered saline solution (PBS) pH:7.4 and suspended at $5 \times 10^7$ cells/ml in the same PBS buffer.

The vaccines were formulated by mixing an infected Sf9 cell homogenate containing $50 \times 10^6$ Sf9 cells expressing each one of recombinant proteins ORF3, ORF5 and ORF7, with an oily adjuvant, or oily phase, composed of a mixture of:

Marcol® 52 . . . 790.0 mg

Simulsol® 5100 . . . 70.0 mg

Montanide® 888 . . . 80.0 mg

Under these conditions, 4 recombinant vaccines were prepared, in doses of 2 ml, composed of 53% antigenic phase and 47% of the oily phase described above, in which the oily phase/antigenic phase relation is a weight/volume relation (W/V). The prepared vaccines presented the following formulation:

1. Vaccine identified as rPRRS C:

53%, by volume, of antigenic phase composed of $50 \times 10^6$ Sf9 cells expressing ORF3; and 47%, by weight, of the oily phase as described above.
2. Vaccine identifed as rPRRS D:
   53%, by volume, of antigenic phase composed of $50 \times 10^6$ Sf9 cells expressing ORF5; and
   47%, by weight, of the oily phase as described above.
3. Vaccine identified as rPRRS E:
   53%, by volume, of antigenic phase composed of $50 \times 10^6$ Sf9 cells expressing ORF7; and
   47%, by weight, of the oily phase as described above.
4. Vaccine identifed as rPRRS F:
   53%, by volume, of antigenic phase composed of $50 \times 10^6$ Sf9 cells expressing ORF3; $50 \times 10^6$ Sf9 cells expressing ORF5, and $50 \times 10^6$ Sf9 cells expressing ORF7, (total $150 \times 10^6$ Sf9 cells); and
   47%, by weight, of the oily phase as described above.

Example 14
Efficacy in Pregnant Sows of $10^{6.1}$ TCID$_{50}$/ml (tissue culture infectious dose 50%) via intranasal route (IN).

For the evaluation of the sows' reproductive results on the day of farrowing, the following data were noted down (Table 3):

no. of piglets born alive and in good health no. of piglets born alive but weak no. of stillborn piglets no. of piglets with partial autolysis (edematous)

no. of mummified piglets piglets alive after the 1st week of life, and piglets alive at the time of weaning (25–30 days of age).

TABLE 3

Reproductive results

NUMBER OF PIGLETS

| SOW No. | VACCINE | TOTAL | BORN ALIVE HEALTHY | BORN ALIVE WEAK | STILL-BORN | PARTIAL AUTOLYS. | MUMMIFIED | PIGLETS ALIVE 1st WEEK | PIGLETS WEANED |
|---|---|---|---|---|---|---|---|---|---|
| 1 | CONTROL | 17 | — | 4 | 9 | 4 | — | — | — |
| 20 | CONTROL | 14 | 9 | — | 2 | 3 | — | 7 | 4 |
| 400398 | rPRRS C | 8 | 8 | — | — | — | — | 7 | 6 |
| 400298 | rPRRS C | 11 | 10 | 1 | — | — | — | 8 | 7 |
| 400118 | rPRRS D | 12 | 6 | 1 | 2 | 3 | — | 5 | 4 |
| 400307 | rPRRS D | 10 | 9 | — | 1 | — | — | 9 | 7 |
| 314010 | rPRRS E | 12 | — | 10 | 1 | 1 | — | 3 | 2 |
| 313426 | rPRRS E | 6 | 3 | — | — | 1 | 2 | 3 | 3 |
| 400059 | rPRRS E | 12 | 6 | 2 | 2 | 2 | — | 1 | 0 |
| 313524 | rPRRS F | 11 | 10 | — | 1 | — | — | 10 | 8 |
| 401236 | rPRRS F | 2 | — | — | — | — | — | 2 | 2 |
| 401426 | rPRRS F | 15 | 12 | 3 | — | — | — | 10 | 10 |

This trial was carried out to evaluate the efficacy of the recombinant vaccines prepared as described in Example 13. To that end, a total of 12 sows—a Landrace X Large White cross—was used. The animals were transferred to the safety stables of the research center.

Two sows were chosen at random (sows no. 400398 and 400298) and were vaccinated with the vaccine identified as rPRRS C. Two sows (sows no. 400118 and 400307) were vaccinated with the vaccine identified as rPRRS D. With the vaccine identified as rPRRS E three sows were vaccinated (sows no. 314010, 313426 and 400059), and with the vaccine identified as rPRRS F three sows were vaccinated (sows no. 313524, 401236 and 401426). The two remaining sows (sows no. 1 and 20) were not vaccinated and were used as control animals.

The sows were vaccinated via deep intramuscular route (IM) in the neck, close to the ear, with a dose of 2 ml of vaccine, and revaccinated 21 days later with the same dose.

Local and general reactions were observed, such as: rectal temperature, feed intake and clinical signs both post-vaccination and post-challenge. Additionally, reproductive post-challenge results in the sows were monitored, as well as the serological results both in sows and piglets. The analysis of the results was used in the evaluation of the efficacy of the vaccine (Table 1).

Challenge was done in the safety stables of the research center. All the animals were infected at the rate of 5 ml of PRRSV-218-P6-Mφ-F22055-29/10/94, a strain isolated and maintained at the deposits of the research center, with a titer Then, serological response was analyzed in the sows (Table 4) and piglets (Tables 5, 6, 7, 8 and 9) by means of a peroxidase monolayer assay (IPMA) [Immuno Peroxidase Monolayer Assay, Wensvoort et al., Vet. Quarterly, Vol. 13, no. 3 (July 1991)], in accordance with the following program:

D 0 (Day 0): Bleeding and vaccination

D+14: Bleeding [at 14 days post-vaccination]

D+21: Bleeding and revaccination [21 days post-vaccination]

D+28: Bleeding [28 days post-vaccination]

D+35: Bleeding [35 days post-vaccination]

D I: Bleeding and challenge

D I+7: Bleeding [at 7 days post-infection]

Serological results in the sows (anti-PRRSV antibodies) are shown in Table 4.

TABLE 4

Serological results (anti-PRRSV antibodies)

| Vaccine | Sow | D 0 | D + 14 | D + 21 | D + 28 | D + 35 | D I | D I + 7 |
|---|---|---|---|---|---|---|---|---|
| rPRRS C | 400298 | − | 320 | 320 | NT | 160 | 320 | ≧640 |
| rPRRS C | 400398 | − | − | − | NT | − | − | ≧640 |
| rPRRS D | 400307 | − | − | − | − | − | − | ≧640 |
| rPRRS D | 400118 | − | − | − | − | − | − | ≧640 |
| rPRRS E | 314010 | − | ≧640 | ≧640 | ≧640 | ≧640 | 160 | 320–640 |
| rPRRS E | 313426 | − | ≧640 | ≧640 | ≧640 | ≧640 | 320 | ≧640 |
| rPRRS E | 400059 | − | ≧640 | 320 | NT | ≧640 | ≧640 | ≧640 |
| rPRRS F | 313524 | − | 320–640 | 320 | ≧640 | ≧640 | 320–640 | ≧640 |
| rPRRS F | 401236 | − | ≧640 | ≧640 | ≧640 | ≧640 | ≧640 | 320 |
| rPRRS F | 401426 | − | 320 | NT | NT | 320 | 160 | ≧640 |
| CONTROL | 1 | − | NT | NT | NT | NT | − | 160 |
| CONTROL | 20 | − | NT | NT | NT | NT | − | 80 |

[NT: Not tested; −: Negative]

TABLE 5

Serological results obtained in the piglets born to control animals (unvaccinated)

| | | BEFORE WEANING | | | WEANING | | POST-WEANING | | | |
|---|---|---|---|---|---|---|---|---|---|---|
| SOW No. | No. | AGE DAYS | REP | Ab | No. | AGE DAYS | No. | AGE DAYS | REF | Ab |
| 1 | 2 | 2 | 1 | ≧640 | 0 | − | 0 | − | | |
| | | | 2 | ≧640 | | | | | | |
| 20 | 7 | 12 | 436 | 320 | 4 | 33 | 3 | 39 | | |
| | | | 437 | 320 | | | | | 437 | 320 |
| | | | 438 | 320 | | | | | 438 | 320–640 |
| | | | 439 | ≧640 | | | | | | |
| | | | 440 | 160 | | | | | | |
| | | | 441 | 320–640 | | | | | 441 | ≧640 |
| | | | 442 | ≧640 | | | | | | |

Sow No.: Reference of the sow.
No.: Number of piglets;
Ab: Antibodies;
−: Negative
Ref: Reference of the piglet.

TABLE 6

Serological results obtained in the piglets born to animals vaccinated with rPRRS C (CRF3)

| | | BEFORE WEANING | | | WEANING | | POST-WEANING | | | |
|---|---|---|---|---|---|---|---|---|---|---|
| SOW No. | No. | AGE DAYS | REF | Ab | No. | AGE DAYS | No. | AGE DAYS | REF | Ab |
| 400398 | 8 | | | N.T. | 7 | | 6 | | | N.T. |
| 400298 | 8 | 7 | 482 | 160 | 7 | 28 | 6 | 42 | 482 | − |
| | | | 483 | 160 | | | | | 483 | − |
| | | | 484 | ≧640 | | | | | 484 | N.T. |
| | | | 485 | 320–640 | | | | | 485 | − |
| | | | 486 | ≧640 | | | | | 486 | − |
| | | | 487 | 320 | | | | | 487 | − |
| | | | 488 | 80 | | | | | | |
| | | | 489 | 160 | | | | | | |

Sow No.: Reference of the sow
No.: Number of piglets;
Ab: Antibodies;
N.T.: Not tested;
−: Negative
Ref: Reference of the piglet

TABLE 7

Serological results obtained in the piglets born to animals vaccinated with rPRRS D (ORF5)

| | | | BEFORE WEANING | | | WEANING | | POST-WEANING | | |
|---|---|---|---|---|---|---|---|---|---|---|
| SOW No. | No. | AGE DAYS | REF | Ab | No. | AGE DAYS | No. | AGE DAYS | REF | Ab |
| 400118 | 5 | 9 | 415 | ≧640 | 4 | 30 | 3 | 44 | | |
| | | | 416 | 80 | | | | | | |
| | | | 417 | 320 | | | | | 417 | – |
| | | | 418 | 80–160 | | | | | 418 | – |
| | | | 419 | 160 | | | | | 419 | – |
| 400307 | 9 | 4 | 424 | 160 | 7 | 25 | 7 | 30 | 424 | – |
| | | | 425 | ≧640 | | | | | 425 | – |
| | | | 426 | ≧640 | | | | | 426 | – |
| | | | 427 | – | | | | | 427 | N.T. |
| | | | 428 | 160 | | | | | 428 | – |
| | | | 429 | 320–640 | | | | | 429 | 80–160 |
| | | | 430 | – | | | | | | |
| | | | 431 | 160 | | | | | | |
| | | | 432 | ≧640 | | | | | 432 | – |

Sow No.: Reference of the sow.
No.: Number of piglets;
Ab: Antibodies;
N.T.: Not tested;
–: Negative
Ref: Reference of the piglet

TABLE 8

Serological results obtained in the piglets born to animals vaccinated with rPRRS E (ORF7)

| | | | BEFORE WEANING | | | WEANING | | POST-WEANING | | |
|---|---|---|---|---|---|---|---|---|---|---|
| SOW No. | No. | AGE DAYS | REF | Ab | No. | AGE DAYS | No. | AGE DAYS | REF | Ab |
| 314010 | 2 | 10 | 411 | 80 | 2 | 31 | 1 | 45 | | |
| | | | 412 | 320 | | | | | 412 | 160 |
| 313426 | 3 | 2 | 421 | ≧640 | 3 | 30 | 3 | 37 | 421 | – |
| | | | 422 | ≧640 | | | | | 422 | 320 |
| | | | 423 | ≧640 | | | | | 423 | 160 |
| 400059 | 4 | 3 | 1 | N.T. | 0 | | | | | |
| | | | 2 | N.T. | | | | | | |
| | | | 3 | N.T. | | | | | | |
| | | | 4 | N.T. | | | | | | |

Sow No.: Reference of the sow.
No.: Number of piglets;
Ab: Antibodies;
N.T.: Not tested;
–: Negative
Ref: Reference of the piglet

TABLE 9

Serological results obtained in the piglets born to animals vaccinated with rPRRS F (ORF3 + 5 + 7)

| | | | BEFORE WEANING | | | WEANING | | POST-WEANING | | |
|---|---|---|---|---|---|---|---|---|---|---|
| SOW No. | No. | AGE DAYS | REF | Ab | No. | AGE DAYS | No. | AGE DAYS | REF | Ab |
| 313524 | 10 | 10 | 401 | ≧640 | 8 | 30 | 8 | 45 | 401 | ≧640 |
| | | | 402 | ≧640 | | | | | 402 | ≧640 |
| | | | 403 | 80–160 | | | | | | |
| | | | 404 | ≧640 | | | | | 404 | ≧640 |
| | | | 405 | ≧640 | | | | | 405 | ≧640 |

TABLE 9-continued

Serological results obtained in the piglets born to animals vaccinated with rPRRS F (ORF3 + 5 + 7)

| | | BEFORE WEANING | | | WEANING | | POST-WEANING | | | |
|---|---|---|---|---|---|---|---|---|---|---|
| SOW No. | No. | AGE DAYS | REF | Ab | No. | AGE DAYS | No. | AGE DAYS | REF | Ab |
| | | | 406 | ≧640 | | | | | 406 | ≧640 |
| | | | 407 | ≧640 | | | | | 407 | 320 |
| | | | 408 | ≧640 | | | | | 408 | ≧640 |
| | | | 409 | ≧640 | | | | | 409 | ≧640 |
| | | | 410 | ≧640 | | | | | | |
| 401236 | 2 | 7 | 413 | ≧640 | 2 | 27 | 2 | 42 | 413 | 80 |
| | | | 414 | ≧640 | | | | | 414 | 80 |
| 401426 | 10 | 11 | 443 | ≧640 | 10 | 32 | 10 | 38 | 443 | – |
| | | | 444 | – | | | | | 444 | – |
| | | | 445 | ≧640 | | | | | 445 | 160 |
| | | | 446 | ≧640 | | | | | 446 | 160 |
| | | | 447 | ≧640 | | | | | 447 | 80 |
| | | | 448 | ≧640 | | | | | 448 | – |
| | | | 449 | ≧640 | | | | | 449 | 160 |
| | | | 450 | 320 | | | | | 450 | – |
| | | | 451 | 160 | | | | | 451 | 80 |
| | | | 452 | 320 | | | | | 452 | – |

Sow No.: Reference of the sow.
No.: Number of piglets;
Ab: Antibodies;
–: Negative
Ref: Reference of the piglet.

With the purpose of assessing the vaccines object of the trial, serological results as well as reproductive results have been evaluated. Table 10 shows some serological data, while Table 11 summarizes the reproductive data of the sows used in the trials, including information on the total number of piglets born, the number of piglets alive after the 1st week, the number of piglets weaned and the number of piglets of over 40 days of age.

TABLE 10

Summary of serological and reproductive data

| | | | SEROCONVERSION [IPMA] | |
|---|---|---|---|---|
| VACCINE | SOW No. | D 0 | POST VAC. | POST INFECTION (7 days) |
| rPRRS C | 400398 | – | – | + |
| rPRRS C | 400298 | – | + | + |
| rPRRS D | 400118 | – | – | + |
| rPRRS D | 400307 | – | – | + |
| rPRRS E | 314010 | – | + | + |
| rPRRS E | 313426 | – | + | + |
| rPRRS E | 400059 | – | + | + |
| rPRRS F | 313524 | – | + | + |
| rPRRS F | 401236 | – | + | + |
| rPRRS F | 401426 | – | + | + |
| CONTROL | 1 | – | – | + |
| CONTROL | 20 | – | – | + |

[–: Negative; +: Positive]
D 0: Time of vaccination

TABLE 11

Summary of reproductive data

| | SOW | NO. OF PIGLETS | | | |
|---|---|---|---|---|---|
| VACCINE | No. | BORN | 1st WEEK | WEANING | >40 DAYS |
| CONTROL | 1 | 17 | 0 | 0 | 0 |
| | 20 | 14 | 7 | 4 | 3 |
| TOTAL | | 31 | 7 | 4 | 3 |
| rPRRS C | 400398 | 8 | 7 | 6 | 6 |
| ORF3 | 400298 | 11 | 8 | 7 | 6 |
| TOTAL | | 19 | 15 | 13 | 12 |
| rPRRS D | 400118 | 12 | 5 | 4 | 3 |
| ORF5 | 400307 | 10 | 9 | 7 | 7 |
| TOTAL | | 22 | 14 | 11 | 10 |
| RPRRS E | 314010 | 12 | 3 | 2 | 1 |
| ORF 7 | 313426 | 6 | 3 | 3 | 3 |
| | 400059 | 12 | 1 | 0 | 0 |
| TOTAL | | 30 | 7 | 5 | 4 |
| RPRRS F | 313524 | 11 | 10 | 8 | 8 |
| ORF | 401236 | 2 | 2 | 2 | 2 |
| 3 + 5 + 7 | 401426 | 15 | 10 | 10 | 9 |
| TOTAL | | 28 | 22 | 20 | 19 |

The results, in their totality, make it clear that in the case of vaccine rPRRS C, one sow serconverted (400298) and one did not (400398); in the case of vaccine D, none of the sows seroconverted; for vaccines E and F there is strong seroconversion due, chiefly, to the protein coded for ORF 7.

There is a favorable behavior in front of challenge, when the vaccinated animals are compared with those not vaccinated, enabling to assert positively that the recombinant vaccines object of the trial constitute an efficacious means for the prevention of PRRS.

It has been verified that vaccinated sows devoid of antibodies titrated with the IPMA technique are protected, which evidences that the said vaccines (rPRRS C and rPRRS D) are capable of inducing cellular immunity.

The efficacy of the vaccine was evaluated by comparing:

a) The percentage of piglets alive after the 1st week in contrast with the total number of piglets born, b) the percentage of weaned piglets in contrast with the total number of piglets born, and c) the percentage of piglets of over 40 days of age in contrast with the total number of piglets born.

Table 12 shows the data relative to the percentage of piglets alive after the 1st week, the percentage of piglets weaned, and the percentage of piglets of over 40 days of age in contrast with the total number of piglets born.

It has been verified that the animals devoid of antibodies, evaluated with the IPMA technique, are protected.

TABLE 12

Percentage of piglets alive after the 1st week, weaned, and of over 40 days in contrast with the total number of piglets born

| VACCINE | % PIGLETS ALIVE 1st WEEK | % PIGLETS WEANED | % PIGLETS >40 DAYS |
|---|---|---|---|
| rPRRS C - ORF 3 | 79% | 68.5% | 63% |
| rPRRS D - ORF 5 | 63.6% | 50% | 45.5% |
| rPRRS E - ORF 7 | 23% | 16.6% | 13.3% |
| rPRRS F - ORF 3 + 5 + 7 | 78.6% | 71.4% | 67.8% |
| CONTROL | 22.5% | 12.9% | 9.6% |

DEPOSIT OF MICROORGANISMS

The recombinant baculoviruses obtained were deposited at the European Collection of Animal Cell Cultures (ECACC), Porton Down, Salisbury, Whiltshire SP4 OJG, United Kingdom. The enomination and accession numbers of the recombinant baculoviruses are:

| Denomination | ECACC Accession Number |
|---|---|
| AcNPV, PRRS2 | V94021007 |
| AcNPV, PRRS3 | V94011325 |
| AcNPV, PRRS4 | V94021008 |

-continued

| Denomination | ECACC Accession Number |
|---|---|
| AcNPV, PRRS5 | V94011326 |
| AcNPV, PRRS6 | V94011327 |
| AcNPV, PRRS7 | V94011328 |

All these baculoviruses were deposited on Jan. 14, 1994, except for AcNPV, PRRS2 (V94021007) and ACNPV, PRRS4 (V94021008) which were deposited on Feb. 10, 1994.

| LEGEND FIGURES | |
|---|---|
| FIG. 3: | |
| a) | PRRSV genome |
| b) | Size (Kb) |
| c) | Clone number |
| FIG. 9: | |
| a) | Antigen titration by ELISA |
| b) | Absorbance at 405 nm |
| c) | Antigen dilutions (1/100) |
| d) | Serum at 1/200 |
| | -------- Field |
| | --+--+-- Experimental |
| | --*--*-- Negative |
| FIG. 10: | |
| a) | Serum titration by ELISA |
| b) | Absorbance at 405 nm |
| c) | Serum dilutions (1/100–1/800) |
| d) | Positive -------- |
| | Negative --+--+-- |
| FIG. 11: | |
| a) | Field sera titration |
| b) | Absorbance at 405 nm |
| c) | Sow sera |

We claim:

1. An isolated protein from the causative virus of porcine reproductive and respiratory syndrome selected from the group consisting of proteins coded by ORFs 2 to 7 of the virus PRRS-Olot.

2. The isolated protein of claim 1 selected from the group consisting of proteins coded by ORFs 3 to 6 of the virus PRRS-Olot.

3. An isolated protein from the causative virus of porcine reproductive and respiratory syndrome comprising at least one amino acid sequence selected from the group consisting of the amino acid sequences depicted in SEQ ID NO:2 through SEQ ID NO:7.

4. The isolated protein of claim 3 comprising at least one amino acid sequence selected from the group consisting of the amino acid sequences depicted in SEQ ID NO:3 through SEQ ID NO:6.

5. The isolated protein of claim 3 comprising a combination of the amino acid sequences of SEQ ID NO:3, SEQ ID NO:5, and SEQ ID NO:7.

6. The isolated protein of claim 4 comprising a combination of the amino acid sequences depicted in SEQ ID NO:3 and SEQ ID NO:5.

7. The isolated protein of claim 4 comprising the amino acid sequence selected from the group consisting of sequences depicted in SEQ ID NO:3 or SEQ ID NO:5.

8. An isolated nucleotide sequence comprising at least one ORF selected from the group consisting of ORFs 2 to 7 of the virus PRRS-Olot.

9. The isolated nucleotide sequence of claim 8 comprising at least one ORF selected from the group consisting of ORFs 3 to 6 of the virus PRRS-Olot.

10. The isolated nucleotide sequence of claim 9 comprising at least one ORF selected from the group consisting of ORF3 to ORF5 of the virus PRRS-Olot.

11. The isolated nucleotide sequence of claim 10 comprising ORF3 of the virus PRRS-Olot.

12. The isolated nucleotide sequence of claim 10 comprising ORF5 of the virus PRRS-Olot.

13. The isolated nucleotide sequence of claim 8 comprising ORF7 of the virus PRRS-Olot.

14. The isolated nucleotide sequence of claim 8 comprising a combination of ORF3, ORF5, and ORF7 of the virus PRRS-Olot.

15. A plasmid comprising at least one nucleotide sequence of claims 8, 9, 10, 11, 12, 13, or 14.

16. The plasmid of claim 15 comprising a combination of the nucleotide sequence of claims 11, 12, and 13.

17. A transfer vector comprising the nucleotide sequences of claims 8, 9, 10, 11, 12, 13, or 14.

18. The transfer vector of claim 17 comprising the nucleotide sequence of claims 11, 12, or 13.

19. The transfer vector of claim 17 further comprising pAcYM1.

20. The transfer vector of claim 18 further comprising pAcYM1.

21. A recombinant expression system comprising the transfer vector of claim 17.

22. The expression system of claim 21 wherein said recombinant expression system is a recombinant baculovirus.

23. The recombinant baculovirus of claim 22 selected from the group consisting of recombinant baculoviruses deposited with the ECACC and having Accession Numbers V94021007, V94011325, V94021008, V94011326, V94011327, and V94011328.

24. The recombinant baculoviruses of claim 23 having ECACC Accession Numbers V94011325, V94011326, and V94011328.

25. A host cell capable of expressing the viral subunit protein encoded by the isolated nucleotide sequence of claims 8, 9, 10, 11, 12, 13, 14.

26. A host cell infected with the recombinant expression system of claim 21.

27. The host cell of claim 26 wherein said host cell is an insect cell and said recombinant expression system is a recombinant baculovirus.

28. A method of expressing isolated viral subunit proteins from the causative agent of porcine reproductive and respiratory syndrome of the virus PRRS-Olot comprising the steps of:
  i) inserting at least one isolated nucleotide sequence selected from the group consisting of ORFs 2 to 7 of PRRS-Olot into suitable transfer vectors;
  ii) transfecting permissive host cells with the transfer vectors so obtained; and
  iii) selecting for recombinant expression systems that express the protein encoded by the corresponding ORF.

29. The method of claim 28 wherein at least one nucleotide sequence is selected from the group consisting of ORFs 3, 5, or 7.

30. The method of claim 28 or 29 wherein the recombinant expression system is a baculovirus.

31. The method of claim 30 wherein the transfer vector is pAcYM1.

32. The method of claim 30 wherein said host cells are insect cells.

33. The method of claim 32 wherein said transfecting step comprises transfecting with a mixture of the transfer vector and DNA of wild-type baculovirus.

34. A recombinant baculovirus obtained by the method of claim 30.

35. A vaccine comprising at least one isolated protein encoded by any of ORFs 3, and 5 of PRRS-Olot and a suitable carrier.

36. An immunogenic composition comprising a cell homogenate containing at least one of the host cells of claim 25.

37. The composition of claim 36 wherein said host cell is an insect cell.

38. An immunogenic composition comprising at least one expression product of recombinant baculovirus of claim 22.

39. An immunogenic composition comprising at least one expression product of recombinant baculovirus of claim 23.

40. The composition of any of claims 35, 36, 37, 38, or 39 further comprising an adjuvant.

41. The composition of claim 40 wherein the adjuvant is oil-based.

42. The composition of claim 41 wherein the adjuvant comprises a mixture of Marcol RTM 52, Simulsol 5100, and Mintanide RTM 888.

43. The composition of claim 36 wherein the adjuvant is aqueous.

44. The composition of any of claim 35, 36, 37, 38, or 39 further comprising a cell response potentiator.

45. The composition of claim 44 further comprising an adjuvant.

46. The composition of claim 44 wherein said cell response potentiator is selected from the group consisting of IL-1, IL-2, IL-4, IL-5, IL-6, IL-12, g-IFN, and cell necrosis factors.

47. The composition of any of claims 35, 36, 37, 38, or 39 further comprising at least one additional porcine pathogen.

48. The composition of claim 47 wherein said porcine pathogen is selected from the group consisting of *Actinobacillus pleuropneumoniae, Haemophilus parasuis, Porcine parvovirus, Leptospira, Escherichia coli, Erysipelothrix rhusiopathiae, Pasteurella multocida, Bordetella bronchiseptica*, Porcine respiratory coronavirus, Rotavirus, pathogens causative of Adjezky's Disease, Swine Influenza or Transmissible Gastroenteritis.

49. The composition of claim 47 further comprising an adjuvant.

50. The composition of claim 47 further comprising a cell response potentiator.

51. A diagnostic kit for the detection of the presence of antibodies that specifically identify PRRSV in a biological sample comprising at least one isolated protein encoded by any of ORFs 2 to 7 of PRRS-Olot and suitable detection means.

52. A diagnostic kit for the detection of the presence of PRRSV in a biological sample comprising antibodies to at least one isolated protein encoded by ORFs 2 to 7 of PRRS-Olot and a suitable detection means.

* * * * *

UNITED STATES PATENT AND TRADEMARK OFFICE
CERTIFICATE OF CORRECTION

PATENT NO. : 5,888,513
DATED : March 30, 1999
INVENTOR(S) : Juan Plana Duran
Jose Ignacio Casal Alvarez
Isabel Climent Sanchez It is certified that error appears in the above-identified patent and that said Letters Patent are hereby corrected as shown below:

Column 1, Line 31 "Proceedngs" should read -- Proceedings

Column 1, Line 46 "Wesvoort" should read -- Wensvoort

Column 1, Line 60 "Cozelmann" should read -- Conzelmann

Column 1, Line 66 "nuceleocapsid" should read -- nucleocapsid

Column 2, Line 14 "Cozelmann" should read -- Conzelmann

Column 2, Line 30 "coraniviruses" should read -- coronaviruses

Column 3, Line 33 "LucKow" should read -- Luckow

Column 3, Line 62 "PPRSV" should read -- PRRSV

Column 4, Line 10 & 11 all should read -- pPRRS

Column 4, Line 39 " (c) " should read -- (c).

Column 4, Line 47 "Jul." should read -- July

UNITED STATES PATENT AND TRADEMARK OFFICE
CERTIFICATE OF CORRECTION

PATENT NO. : 5,888,513

DATED : March 30, 1999

INVENTOR(S) : Juan Plana Duran
Jose Ignacio Casal Alvarez
Isabel Climent Sanchez It is certified that error appears in the above-identified patent and that said Letters Patent are hereby corrected as shown below:

Column 6, Line 6 "inerted" should read -- inserted

Column 7, Line11 "Gen" should read -- Gen.

Column 7, Line 40 "Whiltshire" should read -- Wiltshire

Column 7, Line 50 "recombiant" should read -- recombinant

Column 8, Line 45 "Simulsol" should read --Simulsol [R] --.

Column 9, Line 20 "gastoenteritis" should read -- gastroenteritis

Column 9, Line 35 "serological" should read -- serology

Column 9, Line 55 "aleveolar" should read -- alveolar

Column 9, Line 66 "epiglotis: should read -- epiglottis

Column 10, Line 47 "ith" should read -- with

Column 10, Line 53 and 61 "37° C.," should read -- 37° C,

UNITED STATES PATENT AND TRADEMARK OFFICE
CERTIFICATE OF CORRECTION

PATENT NO.    : 5,888,513

DATED         : March 30, 1999

INVENTOR(S)   : Juan Plana Duran
                Jose Ignacio Casal Alvarez
                Isabel Climent Sanchez It is certified that error appears in the above-identified patent and that said Letters Patent are hereby corrected as shown below:

Column 11, Line 9 "4° C.," should read -- 4° C,

Column 11, Line 18 "polyacrilamide" should read -- polyacrylamide

Column 11, Lines 23-24 "using a covalescent anti-PRRSV serum." should read -- using an anti-PRRSV serum from a convalescent animal.

Column 11, Line 41 "celullose" should read -- cellulose

Column 11, Line 51 "glycongen" should read -- glycogen

Column 11, Line 54 "resuspended" should read -- suspended

Column 11, Line 66 "polyacrilamide" should read -- polyacrylamide

Column 12, Line 8 "synthetize" should read -- synthesized

Column 12, Line 19 "42° C." should read -- 42° C,

Column 12, Line 21 "Rnasa" should read -- Rnase

UNITED STATES PATENT AND TRADEMARK OFFICE
CERTIFICATE OF CORRECTION

PATENT NO.    : 5,888,513
DATED         : March 30, 1999
INVENTOR(S)   : Juan Plana Duran
                Jose Ignacio Casal Alvarez
                Isabel Climent Sanchez It is certified that error appears in the above-identified patent and that said Letters Patent are hereby corrected as shown below:

Column 12, Line 22 - 23 "65° C." should read -- 65° C,

Column 12, Line 24 "37° C." should read -- 37° C,

Column 13, Line 18 "y" should read -- and

Column 13, Line 45 "experiment" should read -- experiments

Column 13, Line 47 "Gen" should read -- Gen.

Column 13, Line 62 "insert the" should read -- insert to the

Column 13, Line 66 "Birnboin" should read -- Birnboim

Column 14, Line 1 "sequenced" should read -- sequencing of

Column 15, Line 11 "accoding" should read -- according

Column 15, Line 11 "Birnboin" should read -- Birnboim

Column 17, Line 9 "27° C." should read -- 27° C,

UNITED STATES PATENT AND TRADEMARK OFFICE
CERTIFICATE OF CORRECTION

PATENT NO. : 5,888,513
DATED : March 30, 1999
INVENTOR(S) : Juan Plana Duran
　　　　　　　Jose Ignacio Casal Alvarez
　　　　　　　Isabel Climent Sanchez It is certified that error appears in the above-identified patent and that said Letters Patent are hereby corrected as shown below:

Column 17, Line 22 "polyacrilamide" should read -- polyacrylamide

Column 17, Line 31 "gene's" should read -- genes'

Column 19, Line 13 "elecrophoresis" should read -- electrophoresis

Column 19, Line 55 "15° C." should read -- 15° C,

Column 20, Line 11 "37° C." should read -- 37° C,

Column 20, Line 44 - 45 "27° C." should read -- 27° C,

Column 21, Line 2 "identifed" should read -- identified

Column 29, Line 35 "Whiltshire" should read -- Wiltshire

Column 29, Line 36 "enomination" should read -- denomination

Column 44, Line 32 "claim" should read -- claims

UNITED STATES PATENT AND TRADEMARK OFFICE
CERTIFICATE OF CORRECTION

PATENT NO. : 5,888,513
DATED : March 30, 1999
INVENTOR(S) : Juan Plana Duran, et al.

It is certified that error appears in the above-indentified patent and that said Letters Patent is hereby corrected as shown below:

Column 44, Line 48 "Adjezky's" should read -- Aujeszky--.

Signed and Sealed this

Eighth Day of May, 2001

Attest:

NICHOLAS P. GODICI

Attesting Officer

Acting Director of the United States Patent and Trademark Office

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
( A ) LENGTH: 3383 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:1:

-continued

| | | | | | |
|---|---|---|---|---|---|
| GAATTGCAGG | TAGAGCTAGG | TAAACCCCGG | CTGCCGCCTG | AGCAAGTGCC | GTGAATCCGA | 60 |
| AGTGATGCAA | TGGGGTCACT | GTGGAGCAAA | ATCAGCCAGC | TGTTCGTGGA | CGCCTTCACT | 120 |
| GAGTTCCTTG | TTAGTGTGGT | TGACATTGTC | ATTTTCCTTG | CCATACTGTT | TGGGTTCACC | 180 |
| GTTGCCGGCT | GGTTACTGGT | CTTTCTTCTC | AGAGTGGTTT | GCTCCGCGCT | TCTCCGTTCG | 240 |
| CGCTCTGCCA | TTCACTCTCC | CGAACTATCG | AAGGTCCTAT | GAAGGCTTGT | TACCCAATTG | 300 |
| CAGACCGGAT | GTCCCACAAT | TCGCTGTCAA | GCACCCATTG | GGTATGTTTT | GGCACATGCG | 360 |
| AGTCTCCCAC | CTAATTGATG | AAATGGTCTC | TCGTCGCATT | TACCAGACCA | TGGAACATTC | 420 |
| AGGTCAAGCG | GCCTGGAAGC | AGGTGGTTAG | TGAGGCCACT | CTTACAAAGC | TGTCAGGACT | 480 |
| TGATATAGTT | ACTCATTTCC | AACACCTGGC | CGCAGTGGAG | GCGGATTCTT | GCCGCTTTCT | 540 |
| CAGCTCACGA | CTTGTGATGC | TAAAAAATCT | TGCCGTTGGC | AATGTGAGCC | TACAGTACAA | 600 |
| CACCACGTTA | GACCGCGTTG | AGCTCATCTT | CCCTACGCCG | GGTACGAGGC | CCAAGTTGAC | 660 |
| CGATTTCAGA | CAATGGCTCA | TCAGTGTGCA | CGCTTCCATT | TTTTCCTCTG | TAGCTTCATC | 720 |
| TGTTACCTTG | TTCATAGTGC | TTTGGCTTCG | AATTCCAATT | CTACGCTATG | TTTTTGGTTT | 780 |
| CCATTGGCCC | ACGGCAACAC | ATCATTCGAG | CTAACCATCA | ACTACACCAT | ATGTATGCCC | 840 |
| TGCTCTACCA | GTCAAGCGGC | TCACCAAAGA | CTCGAGCCCG | GTCGTAACAT | GTGGTGCAGA | 900 |
| ATAGGGCACG | ACAGGTGTGA | GGAACGTGAC | CATGATGAGT | TGTCAATGTC | CATTCCGTCT | 960 |
| GGGTACGATA | ACCTCAAACT | TGAGGGTTAT | TATGCTTGGC | TGGCCTTTTT | GTCCTTTTCC | 1020 |
| TACGCGGCCC | AATTCCATCC | GGAGTTGTTC | GGAATAGGAA | ACGTGTCGCG | CGTCTTCGTG | 1080 |
| GACAAGCAAC | ACCAGTTCAT | TTGCGCCGAG | CATGATGGAC | GAAATTCAAC | CATATCTACC | 1140 |
| GAATATAACA | TCTCCGCATT | ATATGCGTCG | TACTACCATC | ACCAAATAGA | CGGGGGCAAC | 1200 |
| TGGTTCCATT | TGGAATGGCT | GCGGCCATTC | TTTTCCTCCT | GGCTGGTGCT | CAACATTTCA | 1260 |
| TGGTTTCTGA | GGCGTTCGCC | TGTAAGCCCT | GTTTCTGAC | GCATCTATCA | GATATTAAGA | 1320 |
| CCAACACGAC | CGCGGCTGCC | GGTTTCATGG | TCCTTCAGAA | CATCAATTGT | CTCCGACCTC | 1380 |
| ACGGGGTCTC | AACAGCGCAA | GAGAACATTT | CCTTCGGGAA | GCCGTCTCAA | TGTCGTGAAG | 1440 |
| CCGTCGGTAT | TCCCCAGTAC | ATTACGATAA | CGGCTAATGT | GACCGATGAA | TCGTATTTGT | 1500 |
| ACAACGCGGA | CTTGCTGATG | CTTTCTGCGT | GCCTTTTCTA | CGCTTCAGAA | ATGAGCGAAA | 1560 |
| AAGGCTTCAA | AGTTATCTTT | GGGAACGTCT | CTGGCGTTGT | TTCTGCTTGT | GTCAATTTTA | 1620 |
| CAGATTATGT | GGCCCATGTG | ACCCAACATA | CCCAGCAGCA | TCATCTGGTA | ATTGATCACA | 1680 |
| TTCGGTTGCT | GCATTTCTTG | ACACCATCTA | CAATGAGGTG | GGCTACAACC | ATTGCTTGTT | 1740 |
| TGTTCGCCAT | TCTCTTGGCG | ATATGAGATG | TTCTCACAAA | TTGGGGCGTT | TCTTGACTCC | 1800 |
| TCACTCTTGC | TTCTGGTGGC | TTTTTTTGCT | GTGTACCGGC | TTGTCCTGGT | CCTTTGTCGC | 1860 |
| TGGCGGCAGC | AGCTCGACAT | ACCAATACAT | ATATAACTTA | ACGATATGCG | AGCTGAATGG | 1920 |
| GACCGACTGG | TTGTCCAACC | ATTTTGATTG | GGCAGTCGAG | ACCTTTGTGC | TTTACCCGGT | 1980 |
| TGCCACTCAT | ATCCTCTCAC | TGGGTTTTCT | CACAACAAGC | CATTTTTTTG | ACGCGCTCGG | 2040 |
| TCTCGGCGCT | GTGTCCACTA | TAGGATTTGT | TGGCGGGCGG | TATGTACTCA | GCAGCGTGTA | 2100 |
| CGGCGCTTGT | GCTTTCGCAG | CGTTCGTATG | TTTTGTCATC | CGTGCTGTTA | AAAATTGCAT | 2160 |
| GGCTTTCCGC | TATGCCCACA | CCCGGTTTAC | CAACTTCATT | GTGGACGACC | GGGGAGAAT | 2220 |
| CCATCGGTGG | AAGTCTCCAA | TAGTGGTAGA | GAAATTGGGC | AAAGCTGAAG | TCGGTGGCGA | 2280 |
| CCTTGTCACC | ATCAAACATG | TCGTCCTCGA | AGGGGTTAAA | GCTCAACCCT | TGACGAGGAC | 2340 |
| TTCGGCTGAG | CAATGGGAAG | CCTAGACGAT | TTTTGCAATG | ATTCTACCGC | CGCACAAAAG | 2400 |

```
CTTGTGCTAG  CCTTTAGCAT  TACATATACA  CCTATAATGA  TATACGCCCT  TAAGGTGTCA        2460

CGCGGCCGAC  TCCTGGGGCT  GTTGCACATC  CTAATATTCC  TGAATTGTTC  TTTCACATTC        2520

GGATACATGA  CATATGTGCG  TTTTCAATCC  ACCAACCGTG  TCGCACTTAC  TCTGGGGGCT        2580

GTTGTCGCCC  TTCTGTGGGG  TGTTTACAGC  TTCACAGAGT  CATGGAAGTT  TGTTACTTCC        2640

AGATGCAGAT  TGTGTTGCCT  AGGCCGGCGA  TACATTCTGG  CCCCTGCCCA  TCACGTAGAA        2700

AGTGCTGCAG  GTCTCCATTC  AATCCCAGCG  TCTGGTAACC  GAGCATACGC  TGTGAGAAAG        2760

CCCGGACTAA  CATCAGTGAA  CGGCACTCTA  GTTCCAGGAC  TTCGGAGCCT  CGTGCTGGGC        2820

GGCAAACGAG  CTGTTAAACG  AGGAGTGGTT  AACCTCGTCA  AGTATGGCCG  GTAAAAACCA        2880

GAGCCAGAAG  AAAAAGAAAA  GTGCAGCTCC  GATGGGGAAT  GGCCAGCCAG  TCAATCAACT        2940

GTGCCAGTTG  CTGGGTGCAA  TGATAAAGTC  CCAGCGCCAG  CAACCTAGGG  GAGGACAGGC        3000

CAAAAGAAA   AAGCCTGAGA  AGCCACATTT  TCCCTTAGCT  GCTGAAGATG  ACATCCGGCA        3060

CCACCTCACC  CAGACCGAAC  GTTCCCTCTG  CTTGCAATCG  ATCCAGACGG  CTTTTAATCA        3120

AGGCGCAGGA  ACTGCGTCGC  TTTCATCCAG  CGGGAAGGTC  AGTTTTCAGG  TTGAGTTCAT        3180

GCTGCCGGTT  GCTCATACGG  TGCGCCTGAT  TCGCGTGACT  TCTACATCCG  CCAGTCAGGG        3240

TGCAAGCTAA  TTTGACAGTC  AGGTGAATGG  CCGCGATTGA  CGTGTGGCCT  CTAAGTCACC        3300

TATTCAATTA  GGGCGATCAC  ATGGGGGTCA  AACTTAATCA  GGCAGGAACC  ATGTGACCGA        3360

AATTAAAAAA  AAAAAAAAAA  AAA                                                  3383
```

( 2 ) INFORMATION FOR SEQ ID NO:2:

( i ) SEQUENCE CHARACTERISTICS:
        ( A ) LENGTH: 249 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Met  Gln  Trp  Gly  His  Cys  Gly  Ala  Lys  Ser  Ala  Ser  Cys  Ser  Trp  Thr
 1              5                        10                       15

Pro  Ser  Leu  Ser  Ser  Leu  Leu  Val  Trp  Leu  Thr  Leu  Ser  Phe  Ser  Leu
              20                        25                       30

Pro  Tyr  Cys  Leu  Gly  Ser  Pro  Leu  Pro  Ala  Gly  Tyr  Trp  Ser  Phe  Phe
         35                        40                       45

Ser  Glu  Trp  Phe  Ala  Pro  Arg  Phe  Ser  Val  Arg  Ala  Leu  Pro  Phe  Thr
     50                        55                       60

Leu  Pro  Asn  Tyr  Arg  Arg  Ser  Tyr  Glu  Gly  Leu  Leu  Pro  Asn  Cys  Arg
65                       70                       75                       80

Pro  Asp  Val  Pro  Gln  Phe  Ala  Val  Lys  His  Pro  Leu  Gly  Met  Phe  Trp
                    85                       90                       95

His  Met  Arg  Val  Ser  His  Leu  Ile  Asp  Glu  Met  Val  Ser  Arg  Arg  Ile
              100                      105                      110

Tyr  Gln  Thr  Met  Glu  His  Ser  Gly  Gln  Ala  Ala  Trp  Lys  Gln  Val  Val
         115                      120                      125

Ser  Glu  Ala  Thr  Leu  Thr  Lys  Leu  Ser  Gly  Leu  Asp  Ile  Val  Thr  His
     130                      135                      140

Phe  Gln  His  Leu  Ala  Ala  Val  Glu  Ala  Asp  Ser  Cys  Arg  Phe  Leu  Ser
145                      150                      155                      160

Ser  Arg  Leu  Val  Met  Leu  Lys  Asn  Leu  Ala  Val  Gly  Asn  Val  Ser  Leu
                    165                      170                      175
```

```
Gln Tyr Asn Thr Thr Leu Asp Arg Val Glu Leu Ile Phe Pro Thr Pro
            180                 185                 190

Gly Thr Arg Pro Lys Leu Thr Asp Phe Arg Gln Trp Leu Ile Ser Val
        195                 200                 205

His Ala Ser Ile Phe Ser Ser Val Ala Ser Ser Val Thr Leu Phe Ile
    210                 215                 220

Val Leu Trp Leu Arg Ile Pro Ile Leu Arg Tyr Val Phe Gly Phe His
225                 230                 235                 240

Trp Pro Thr Ala Thr His His Ser Ser
                245
```

( 2 ) INFORMATION FOR SEQ ID NO:3:

( i ) SEQUENCE CHARACTERISTICS:
        ( A ) LENGTH: 265 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

```
Met Ala His Gln Cys Ala Arg Phe His Phe Phe Leu Cys Ser Phe Ile
1               5                   10                  15

Cys Tyr Leu Val His Ser Ala Leu Ala Ser Asn Ser Asn Ser Thr Leu
            20                  25                  30

Cys Phe Trp Phe Pro Leu Ala His Gly Asn Thr Ser Phe Glu Leu Thr
            35                  40                  45

Ile Asn Tyr Thr Ile Cys Met Pro Cys Ser Thr Ser Gln Ala Ala His
        50                  55                  60

Gln Arg Leu Glu Pro Gly Arg Asn Met Trp Cys Arg Ile Gly His Asp
65                  70                  75                  80

Arg Cys Glu Glu Arg Asp His Asp Glu Leu Ser Met Ser Ile Pro Ser
                85                  90                  95

Gly Tyr Asp Asn Leu Lys Leu Glu Gly Tyr Tyr Ala Trp Leu Ala Phe
                100                 105                 110

Leu Ser Phe Ser Tyr Ala Ala Gln Phe His Phe Glu Leu Phe Gly Ile
            115                 120                 125

Gly Asn Val Ser Arg Val Phe Val Asp Lys Gln His Gln Phe Ile Cys
        130                 135                 140

Ala Glu His Asp Gly Arg Asn Ser Thr Ile Ser Thr Glu Tyr Asn Ile
145                 150                 155                 160

Ser Ala Leu Tyr Ala Ser Tyr Tyr His His Gln Ile Asp Gly Gly Asn
                165                 170                 175

Trp Phe His Leu Glu Trp Leu Arg Pro Phe Phe Ser Ser Trp Leu Val
            180                 185                 190

Leu Asn Ile Ser Trp Phe Leu Arg Arg Ser Pro Val Ser Pro Val Ser
        195                 200                 205

Arg Arg Ile Tyr Gln Ile Leu Arg Pro Thr Arg Pro Arg Leu Pro Val
    210                 215                 220

Ser Trp Ser Phe Arg Thr Ser Ile Val Ser Asp Leu Thr Gly Ser Gln
225                 230                 235                 240

Gln Arg Lys Arg Thr Phe Pro Ser Gly Ser Arg Leu Asn Val Val Lys
                245                 250                 255

Pro Ser Val Phe Pro Ser Thr Leu Arg
                260                 265
```

37

-continued ( 2 ) INFORMATION FOR SEQ ID NO:4:

( i ) SEQUENCE CHARACTERISTICS:
        ( A ) LENGTH: 183 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

```
Met Ala Ala Ala Ile Leu Phe Leu Leu Ala Gly Ala Gln His Phe Met
 1               5                  10                  15
Val Ser Glu Ala Phe Ala Cys Lys Pro Cys Phe Ser Thr His Leu Ser
            20                  25                  30
Asp Ile Lys Thr Asn Thr Thr Ala Ala Ala Gly Phe Met Val Leu Gln
        35                  40                  45
Asn Ile Asn Cys Leu Arg Pro His Gly Val Ser Thr Ala Gln Glu Asn
    50                  55                  60
Ile Ser Phe Gly Lys Pro Ser Gln Cys Arg Glu Ala Val Gly Ile Pro
65                  70                  75                  80
Gln Tyr Ile Thr Ile Thr Ala Asn Val Thr Asp Glu Ser Tyr Leu Tyr
                85                  90                  95
Asn Ala Asp Leu Leu Met Leu Ser Ala Cys Leu Phe Tyr Ala Ser Glu
            100                 105                 110
Met Ser Glu Lys Gly Phe Lys Val Ile Phe Gly Asn Val Ser Gly Val
        115                 120                 125
Val Ser Ala Cys Val Asn Phe Thr Asp Tyr Val Ala His Val Thr Gln
    130                 135                 140
His Thr Gln Gln His His Leu Val Ile Asp His Ile Arg Leu Leu His
145                 150                 155                 160
Phe Leu Thr Pro Ser Thr Met Arg Trp Ala Thr Thr Ile Ala Cys Leu
                165                 170                 175
Phe Ala Ile Leu Leu Ala Ile
            180
```

( 2 ) INFORMATION FOR SEQ ID NO:5:

( i ) SEQUENCE CHARACTERISTICS:
        ( A ) LENGTH: 200 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:5:

```
Met Arg Cys Ser His Lys Leu Gly Arg Phe Leu Thr Pro His Ser Cys
 1               5                  10                  15
Phe Trp Trp Leu Phe Leu Leu Cys Thr Gly Leu Ser Trp Ser Phe Val
            20                  25                  30
Ala Gly Gly Ser Ser Ser Thr Tyr Gln Tyr Ile Tyr Asn Leu Thr Ile
        35                  40                  45
Cys Glu Leu Asn Gly Thr Asp Trp Leu Ser Asn His Phe Asp Trp Ala
    50                  55                  60
Val Glu Thr Phe Val Leu Tyr Pro Val Ala Thr His Ile Leu Ser Leu
65                  70                  75                  80
Gly Phe Leu Thr Thr Ser His Phe Phe Asp Ala Leu Gly Leu Gly Ala
                85                  90                  95
Val Ser Thr Ile Gly Phe Val Gly Gly Arg Tyr Val Leu Ser Ser Val
```

|     |     |     |     |     |     |     |     |     |     |     |     |     |     |     |
| --- | --- | --- | --- | --- | --- | --- | --- | --- | --- | --- | --- | --- | --- | --- |
|     |     |     |     | 100 |     |     |     | 105 |     |     |     | 110 |     |     |
| Tyr | Gly | Ala | Cys | Ala | Phe | Ala | Ala | Phe | Val | Cys | Phe | Val | Ile | Arg | Ala |
|     |     |     | 115 |     |     |     |     | 120 |     |     |     | 125 |     |     |
| Val | Lys | Asn | Cys | Met | Ala | Cys | Arg | Tyr | Ala | His | Thr | Arg | Phe | Thr | Asn |
|     |     | 130 |     |     |     |     | 135 |     |     |     |     | 140 |     |     |
| Phe | Ile | Val | Asp | Asp | Arg | Gly | Arg | Ile | His | Arg | Trp | Lys | Ser | Pro | Ile |
| 145 |     |     |     |     | 150 |     |     |     |     | 155 |     |     |     |     | 160 |
| Val | Val | Glu | Lys | Leu | Gly | Lys | Ala | Glu | Val | Gly | Gly | Asp | Leu | Val | Thr |
|     |     |     |     | 165 |     |     |     |     | 170 |     |     |     |     | 175 |     |
| Ile | Lys | His | Val | Val | Leu | Glu | Gly | Val | Lys | Ala | Gln | Pro | Leu | Thr | Arg |
|     |     |     | 180 |     |     |     |     | 185 |     |     |     |     | 190 |     |     |
| Thr | Ser | Ala | Glu | Gln | Trp | Glu | Ala |     |     |     |     |     |     |     |     |
|     |     | 195 |     |     |     |     | 200 |     |     |     |     |     |     |     |     |

( 2 ) INFORMATION FOR SEQ ID NO:6:

( i ) SEQUENCE CHARACTERISTICS:
        ( A ) LENGTH: 173 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:6:

|     |     |     |     |     |     |     |     |     |     |     |     |     |     |     |     |
| --- | --- | --- | --- | --- | --- | --- | --- | --- | --- | --- | --- | --- | --- | --- | --- |
| Met | Gly | Ser | Leu | Asp | Asp | Phe | Cys | Asn | Asp | Ser | Thr | Ala | Ala | Gln | Lys |
| 1   |     |     |     | 5   |     |     |     |     | 10  |     |     |     |     | 15  |     |
| Leu | Val | Leu | Ala | Phe | Ser | Ile | Thr | Tyr | Thr | Pro | Ile | Met | Ile | Tyr | Ala |
|     |     |     | 20  |     |     |     |     | 25  |     |     |     |     | 30  |     |     |
| Leu | Lys | Val | Ser | Arg | Gly | Arg | Leu | Leu | Gly | Leu | Leu | His | Ile | Leu | Ile |
|     |     | 35  |     |     |     |     | 40  |     |     |     |     | 45  |     |     |     |
| Phe | Leu | Asn | Cys | Ser | Phe | Thr | Phe | Gly | Tyr | Met | Thr | Tyr | Val | Arg | Phe |
|     | 50  |     |     |     |     | 55  |     |     |     |     | 60  |     |     |     |     |
| Gln | Ser | Thr | Asn | Arg | Val | Ala | Leu | Thr | Leu | Gly | Ala | Val | Val | Ala | Leu |
| 65  |     |     |     |     | 70  |     |     |     |     | 75  |     |     |     |     | 80  |
| Leu | Trp | Gly | Val | Tyr | Ser | Phe | Thr | Glu | Ser | Trp | Lys | Phe | Val | Thr | Ser |
|     |     |     |     | 85  |     |     |     |     | 90  |     |     |     |     | 95  |     |
| Arg | Cys | Arg | Leu | Cys | Cys | Leu | Gly | Arg | Arg | Tyr | Ile | Leu | Ala | Pro | Ala |
|     |     |     | 100 |     |     |     |     | 105 |     |     |     |     | 110 |     |     |
| His | His | Val | Glu | Ser | Ala | Ala | Gly | Leu | His | Ser | Ile | Pro | Ala | Ser | Gly |
|     |     | 115 |     |     |     |     | 120 |     |     |     |     | 125 |     |     |     |
| Asn | Arg | Ala | Tyr | Ala | Val | Arg | Lys | Pro | Gly | Leu | Thr | Ser | Val | Asn | Gly |
|     | 130 |     |     |     |     | 135 |     |     |     |     | 140 |     |     |     |     |
| Thr | Leu | Val | Pro | Gly | Leu | Arg | Ser | Leu | Val | Leu | Gly | Gly | Lys | Arg | Ala |
| 145 |     |     |     |     | 150 |     |     |     |     | 155 |     |     |     |     | 160 |
| Val | Lys | Arg | Gly | Val | Val | Asn | Leu | Val | Lys | Tyr | Gly | Arg |     |     |     |
|     |     |     |     | 165 |     |     |     |     | 170 |     |     |     |     |     |     |

( 2 ) INFORMATION FOR SEQ ID NO:7:

( i ) SEQUENCE CHARACTERISTICS:
        ( A ) LENGTH: 128 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:7:

|     |     |     |     |     |     |     |     |     |     |     |     |     |     |     |     |
| --- | --- | --- | --- | --- | --- | --- | --- | --- | --- | --- | --- | --- | --- | --- | --- |
| Met | Ala | Gly | Lys | Asn | Gln | Ser | Gln | Lys | Lys | Lys | Lys | Ser | Ala | Ala | Pro |

```
        1               5                       10                      15
     Met Gly Asn Gly Gln Pro Val Asn Gln Leu Cys Gln Leu Leu Gly Ala
                  20                  25                  30
     Met Ile Lys Ser Gln Arg Gln Gln Pro Arg Gly Gly Gln Ala Lys Lys
              35                  40                  45
     Lys Lys Pro Glu Lys Pro His Phe Pro Leu Ala Ala Glu Asp Asp Ile
          50                  55                  60
     Arg His His Leu Thr Gln Thr Glu Arg Ser Leu Cys Leu Gln Ser Ile
     65                  70                  75                      80
     Gln Thr Ala Phe Asn Gln Gly Ala Gly Thr Ala Ser Leu Ser Ser Ser
                      85                  90                  95
     Gly Lys Val Ser Phe Gln Val Glu Phe Met Leu Pro Val Ala His Thr
                  100                 105                 110
     Val Arg Leu Ile Arg Val Thr Ser Thr Ser Ala Ser Gln Gly Ala Ser
                  115                 120                 125
```

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

CGGGCTCGAG CCTTTGGCGA                        20

( 2 ) INFORMATION FOR SEQ ID NO:9:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

GTAAAACGAC GGCCAGT                          17

( 2 ) INFORMATION FOR SEQ ID NO:10:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

AACAGCTATG ACCATG                           16